US012310845B2

(12) United States Patent
Benichou et al.

(10) Patent No.: US 12,310,845 B2
(45) Date of Patent: *May 27, 2025

(54) DOCKING ELEMENTS

(71) Applicant: TRULEAF MEDICAL LTD., Caesarea (IL)

(72) Inventors: Netanel Benichou, Hof Carmel (IL); Benjamin Spenser, Hof Carmel (IL); Moran Sobol, Haifa (IL)

(73) Assignee: TRULEAF MEDICAL LTD., Caesarea (IL)

( * ) Notice: Subject to any disclaimer, the term of this patent is extended or adjusted under 35 U.S.C. 154(b) by 726 days.

This patent is subject to a terminal disclaimer.

(21) Appl. No.: 17/485,624

(22) Filed: Sep. 27, 2021

(65) Prior Publication Data
US 2022/0008195 A1    Jan. 13, 2022

Related U.S. Application Data

(62) Division of application No. 16/498,065, filed as application No. PCT/IL2018/050229 on Mar. 1, 2018, now Pat. No. 11,160,653.

(Continued)

(51) Int. Cl.
*A61F 2/24*    (2006.01)
*A61F 2/00*    (2006.01)

(52) U.S. Cl.
CPC .......... *A61F 2/2409* (2013.01); *A61F 2/0077* (2013.01); *A61F 2/2418* (2013.01);
(Continued)

(58) Field of Classification Search
None
See application file for complete search history.

(56) References Cited

U.S. PATENT DOCUMENTS 5,332,402 A * 7/1994 Teitelbaum ........... A61F 2/2424
                                                  623/2.35
7,291,168 B2   11/2007 Macoviak et al.
(Continued)

FOREIGN PATENT DOCUMENTS

WO    2011/057087 A1   5/2011
WO    2015/173794 A1   11/2015
(Continued)

OTHER PUBLICATIONS

Cismaru, et al (Cismaru), "Distance between the Left Atrial Appendage and Mitral Annulus Evaluated by CARTO 3 Integrated Computed Tomography Imaging", Medical Principles and Practice, Oct. 2015, 24(6): 555-559. (Year: 2015).*
(Continued)

*Primary Examiner* — Leslie A Lopez
(74) *Attorney, Agent, or Firm* — Sughrue Mion, PLLC

(57) ABSTRACT

Apparatus and methods are described for treating a subject with a diseased atrioventricular valve. A docking element is implanted within the subject's atrium such that no portion of the docking element extends through the subject's atrioventricular valve. The docking becomes anchored to tissue of the atrium at least partially via ingrowth of the tissue of the atrium. The docking element includes a ring, which is implanted at the annulus of the atrioventricular valve, and a frame having a height of at least 15 mm, which extends upwardly from the ring. A prosthetic atrioventricular valve apparatus is placed at least partially inside the docking element subsequent to the ingrowth of the tissue of the atrium having occurred, and becomes anchored to the docking element, at least partially by radially expanding against the ring. Other applications are also described.

14 Claims, 11 Drawing Sheets

Related U.S. Application Data

(60) Provisional application No. 62/476,989, filed on Mar. 27, 2017.

(52) U.S. Cl.
CPC ............. *A61F 2002/0086* (2013.01); *A61F 2220/0016* (2013.01)

(56) References Cited

U.S. PATENT DOCUMENTS

| | | | |
|---|---|---|---|
| 8,408,214 | B2 | 4/2013 | Spenser |
| 8,454,686 | B2 | 6/2013 | Alkhatib |
| 8,828,043 | B2 | 9/2014 | Chambers |
| 8,870,950 | B2 | 10/2014 | HaCohen |
| 8,888,843 | B2 | 11/2014 | Khairkhahan et al. |
| 8,992,604 | B2 | 3/2015 | Gross et al. |
| 9,011,515 | B2 | 4/2015 | Schweich, Jr. et al. |
| 9,017,399 | B2 | 4/2015 | Gross et al. |
| 9,241,792 | B2 | 1/2016 | Benichou et al. |
| 9,326,852 | B2 | 5/2016 | Spenser |
| 9,387,078 | B2 | 7/2016 | Gross et al. |
| 9,414,823 | B2 | 8/2016 | Ben Hamou et al. |
| 9,566,152 | B2 | 2/2017 | Schweich, Jr. et al. |
| 9,622,862 | B2 | 4/2017 | Lashinski et al. |
| 2004/0138745 | A1* | 7/2004 | Macoviak ............ A61F 2/2454 623/2.14 |
| 2005/0228468 | A1* | 10/2005 | Macoviak .......... A61B 18/1492 607/119 |
| 2006/0052804 | A1 | 3/2006 | Miahle |
| 2006/0178700 | A1* | 8/2006 | Quinn .................... A61F 2/246 606/213 |
| 2007/0066993 | A1* | 3/2007 | Kreidler ........... A61B 17/12122 606/213 |
| 2007/0156233 | A1* | 7/2007 | Kapadia ................ A61F 2/2418 623/2.11 |
| 2008/0004534 | A1* | 1/2008 | Gelbart .................. A61B 5/028 607/122 |
| 2008/0208327 | A1* | 8/2008 | Rowe .................... A61F 2/2427 604/509 |
| 2008/0215085 | A1 | 9/2008 | Whisenant et al. |
| 2009/0281609 | A1 | 11/2009 | Benichou et al. |
| 2010/0049315 | A1 | 2/2010 | Kirson |
| 2010/0204785 | A1 | 8/2010 | Alkhatib |
| 2011/0071623 | A1 | 3/2011 | Finch et al. |
| 2011/0137410 | A1 | 6/2011 | Hacohen |
| 2011/0224785 | A1 | 9/2011 | Hacohen |
| 2012/0022633 | A1 | 1/2012 | Olson et al. |
| 2012/0022639 | A1 | 1/2012 | Hacohen et al. |
| 2012/0022640 | A1 | 1/2012 | Gross et al. |
| 2012/0083832 | A1 | 4/2012 | Delaloye et al. |
| 2012/0253386 | A1 | 10/2012 | Rowe et al. |
| 2013/0006352 | A1 | 1/2013 | Yaron |
| 2013/0035759 | A1 | 2/2013 | Gross et al. |
| 2014/0025164 | A1 | 1/2014 | Montorfano et al. |
| 2014/0031928 | A1 | 1/2014 | Murphy et al. |
| 2014/0207231 | A1 | 7/2014 | Hacohen et al. |
| 2014/0222136 | A1 | 8/2014 | Geist et al. |
| 2014/0243966 | A1 | 8/2014 | Garde et al. |
| 2014/0277390 | A1 | 9/2014 | Ratz et al. |
| 2014/0309730 | A1 | 10/2014 | Alon et al. |
| 2014/0324164 | A1 | 10/2014 | Gross et al. |
| 2014/0358222 | A1 | 12/2014 | Gorman, III et al. |
| 2014/0379074 | A1 | 12/2014 | Spence et al. |
| 2015/0045880 | A1 | 2/2015 | Hacohen |
| 2015/0157457 | A1 | 6/2015 | Hacohen |
| 2015/0173898 | A1 | 6/2015 | Drasler et al. |
| 2015/0209136 | A1 | 7/2015 | Braido et al. |
| 2015/0216661 | A1 | 8/2015 | HaCohen et al. |
| 2015/0351906 | A1 | 12/2015 | Hammer et al. |
| 2015/0359629 | A1 | 12/2015 | Ganesan et al. |
| 2016/0106539 | A1 | 4/2016 | Buchbinder et al. |
| 2016/0213473 | A1 | 7/2016 | Hacohen et al. |
| 2016/0242905 | A1 | 8/2016 | Chambers |
| 2016/0296330 | A1 | 10/2016 | Hacohen |
| 2016/0302920 | A1 | 10/2016 | Al-Jilaihawi |
| 2016/0310274 | A1 | 10/2016 | Gross et al. |
| 2016/0324633 | A1 | 11/2016 | Gross et al. |
| 2016/0346084 | A1 | 12/2016 | Taylor et al. |
| 2016/0367365 | A1 | 12/2016 | Conklin |
| 2018/0042719 | A1 | 2/2018 | Chambers et al. |
| 2018/0042720 | A1 | 2/2018 | Chambers |
| 2018/0042721 | A1 | 2/2018 | Chambers |
| 2018/0133009 | A1 | 5/2018 | Alon |
| 2018/0168804 | A1 | 6/2018 | Nguyen et al. |
| 2018/0200049 | A1 | 7/2018 | Chambers et al. |
| 2018/0206988 | A1 | 7/2018 | Chambers |
| 2018/0256329 | A1* | 9/2018 | Chambers ............ A61F 2/2409 |
| 2018/0360602 | A1 | 12/2018 | Kumar |
| 2019/0167409 | A1 | 6/2019 | Genereux |
| 2019/0175111 | A1 | 6/2019 | Genereux et al. |
| 2019/0201192 | A1 | 7/2019 | Kruse et al. |
| 2019/0209320 | A1 | 7/2019 | Drasler et al. |
| 2019/0216597 | A1 | 7/2019 | Chambers |
| 2019/0247191 | A1 | 8/2019 | Chambers et al. |
| 2019/0365538 | A1 | 12/2019 | Chambers et al. |
| 2020/0093599 | A1 | 3/2020 | Benichou |
| 2021/0113330 | A1 | 4/2021 | Benichou et al. |

FOREIGN PATENT DOCUMENTS

| | | |
|---|---|---|
| WO | 2015/188066 A1 | 12/2015 |
| WO | 2016/134239 A1 | 8/2016 |
| WO | 2018/031855 A1 | 2/2018 |
| WO | 2018/031857 A1 | 2/2018 |
| WO | 2018/031862 A1 | 2/2018 |
| WO | 2018/136726 A1 | 7/2018 |
| WO | 2018/140374 A1 | 8/2018 |
| WO | 2018/165225 A1 | 9/2018 |
| WO | 2018/178966 A1 | 10/2018 |
| WO | 2018/232118 A1 | 12/2018 |
| WO | 2019/112983 A1 | 6/2019 |
| WO | 2019/112985 A1 | 6/2019 |
| WO | 2019/136040 A1 | 7/2019 |
| WO | 2019/157480 A1 | 8/2019 |
| WO | 2021/064624 A1 | 4/2021 |

OTHER PUBLICATIONS

International Search Report and Written Opinion from PCT/IL2018/050229 dated May 9, 2018.
Invitation to pay Additional Fees for PCT Application No. PCT/IB2020/059195 mailed on Dec. 14, 2020.
International Search Report and Written Opinion for PCT Application No. PCT/IB2020/059195 mailed on Feb. 4, 2021.
A Restriction Requirement issued on Nov. 24, 2020 for U.S. Appl. No. 16/580,319.
Extended European Search Report issued for EP 19199161.1 on Dec. 4, 2019.
International Search Report and Written Opinion from PCT/IL2018/050230 dated May 22, 2018.
Preston-Maher, et al.; "A Technical Review of Minimally Invasive Mitral Valve Replacements", Cardiovascular Engineering Technology, 2015, vol. 6, No. 2, pp. 174-184.
Office Action dated Mar. 18, 2021 in U.S. Appl. No. 16/580,319.
Office Action dated Feb. 25, 2021 in U.S. Appl. No. 16/498,099.
Cismaru, et al., "Distance between the Left Atrial Appendage and Mitral Annulus Evaluated by CARTO 3 Integrated Computed Tomography Imaging", Medical Principles and Practice, Oct. 2015, 24(6): 555-559. (Year: 2015).
Restriction Requirement issued on Feb. 10, 2021 for U.S. Appl. No. 16/498,065.
Office Action issued on Apr. 27, 2021 for U.S. Appl. No. 16/498,065.
Non-Final Office Action dated Oct. 14, 2021 which issued during the prosecution of U.S. Appl. No. 16/580,319.

* cited by examiner

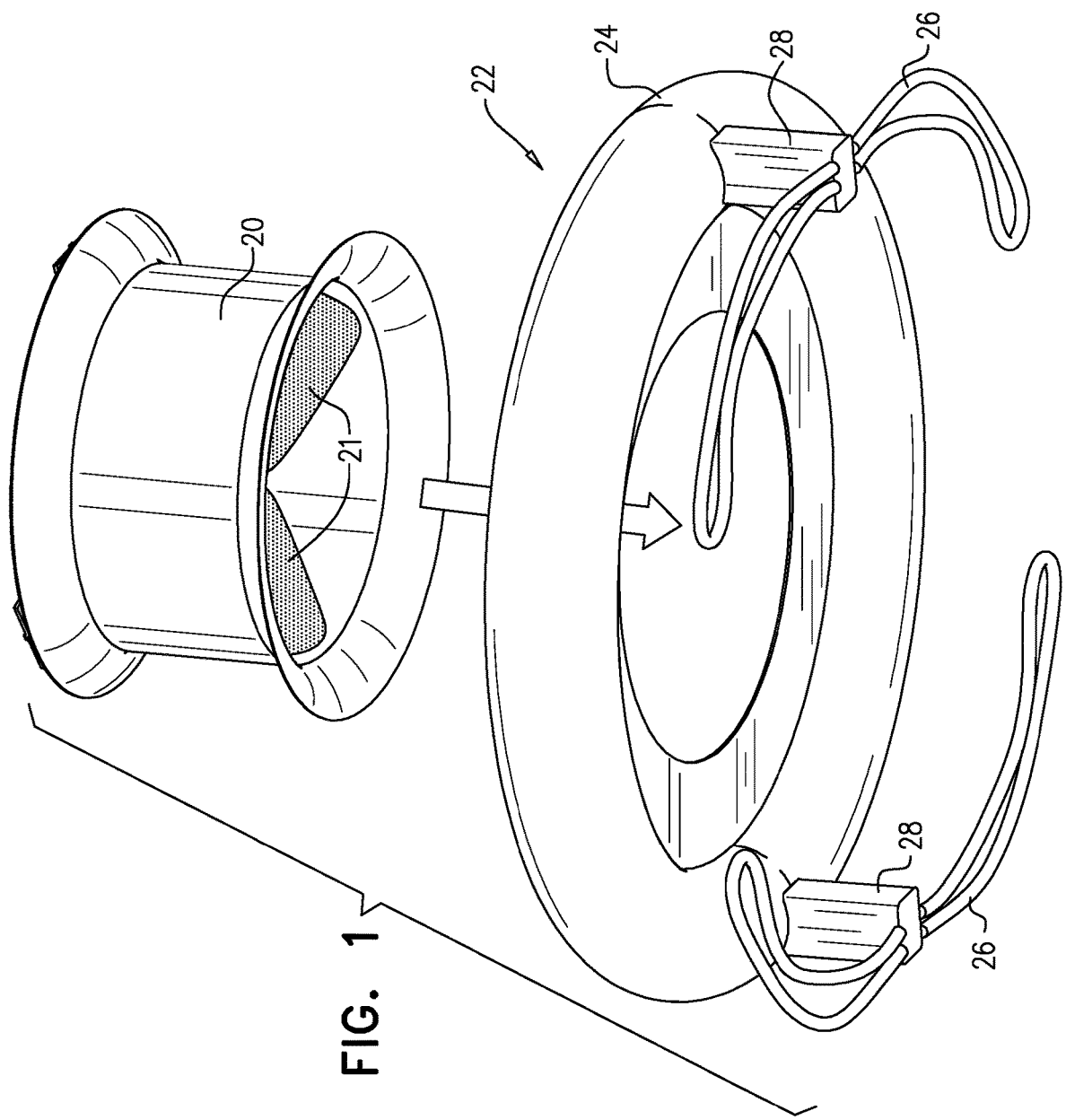

DOCKING ELEMENTS

CROSS-REFERENCE TO RELATED APPLICATIONS

The present application is a divisional of U.S. patent application Ser. No. 16/498,065 to Benichou (published as US 2021/0113330), filed Sep. 26, 2019, which is the US national phase application of PCT Application No. PCT/IL/2018/050229 to Benichou (published as WO 18/178966), filed Mar. 1, 2018, which claims priority from U.S. Provisional Application 62/476,989 to Benichou, entitled "Docking element," filed Mar. 27, 2017, which is incorporated herein by reference.

FIELD OF EMBODIMENTS OF THE INVENTION

Some applications of the present invention generally relate to medical apparatus and methods. Specifically, some applications of the present invention relate to apparatus and methods for use with a prosthetic mitral valve.

BACKGROUND

Atrioventricular valves are cardiac valves that prevent backflow from the ventricles into the atria during systole. They are anchored to the wall of the heart at the fibrous skeleton by anchoring tendons named chordae tendineae. The chordae tendineae are attached to papillary muscles. Together, the papillary muscles and the chordae tendineae keep the valves from prolapsing into the atria when they close during systole. The actual opening and closing of the valves is caused by a pressure gradient across the valve. The left-side atrioventricular valve is a bicuspid valve having two leaflets, and is commonly known as the mitral valve. The right-side atrioventricular valve is a tricuspid valve, having three leaflets. Both of these valves may be damaged and dysfunctional, resulting in leakage during systole, requiring the valves to be repaired or replaced.

While the mitral valve is generally an ellipse or D-shaped, the tricuspid valve is more circular. The left ventricle pumps oxygenated blood around the body and so the mitral valve has to withstand a higher pressure than the tricuspid valve which only has to pump deoxygenated blood to the nearby lungs.

Occasionally, the mitral valve is congenitally abnormal or destroyed by infection or a bacterial endocarditis. More often, the mitral valve becomes degenerative with age, or as a result of rheumatic fever. There are different valvular heart disorders associated with the mitral valve such as mitral stenosis and mitral regurgitation. In the case of mitral stenosis, the valve orifice, i.e., the cross-section available for blood passage is reduced because of calcium nodes, leaflet thickening and/or reduced leaflet mobility, and, consequently, the valve does not allow normal blood flow. To overcome the damaged valve and to transport the same amount of blood, the left atrium requires a higher pressure than normal. The constant pressure overload of the left atrium may cause it to increase in size and become more prone to develop atrial fibrillation and to lose the atrial kick. The loss of the atrial kick due to atrial fibrillation can cause a precipitous decrease in cardiac output. A reduction in cardiac output, associated with acceleration of heart rate and shortening of the diastolic time, frequently leads to congestive heart failure. In most cases, mitral stenosis is due to rheumatic heart disease. The treatment options for mitral stenosis include medical management, surgical repair, surgical replacement of the valve, and percutaneous balloon valvuloplasty.

Mitral regurgitation causes heart murmurs and may have severe physiological consequences. Mitral regurgitation is caused either by ischemic heart disease (such cases being called "ischemic mitral regurgitation"), or mitral valve prolapse. Ischemic mitral regurgitation is a result of ventricular remodeling which is secondary to ischemic heart disease. The heart's posterior wall, which is not attached to the heart's fibrous skeleton, dilates. As a result of the change of the left ventricular geometry, the posterior leaflet, which is attached to the posterior heart wall, is displaced and misaligned from the anterior leaflet which results in mitral regurgitation.

Mitral valve prolapse is a condition caused by degeneration of the valve's connective tissue. Patients with classic mitral valve prolapse have surplus connective tissue. This weakens the leaflets and adjacent tissue, resulting in increased leaflet area and elongation of the chordae tendineae. Elongation of the chordae tendineae often causes rupture. Tweaked leaflets may be displaced in some portion of one or both of the abnormally thickened mitral valve leaflets into the left atrium during systole. Advanced lesions lead to leaflet folding, inversion, and displacement toward the left atrium. The abnormal leaflet structure leads to incomplete closure of the mitral valve and consequent mitral regurgitation.

In mitral regurgitation, the heart has to work harder by pumping not only the regular volume of blood, but also the extra volume of blood that is regurgitated back into the left atrium. The added workload creates an excessive strain on the left ventricle, which can lead to heart failure.

While patients with mild to moderate mitral regurgitation caused by mitral valve prolapse might experience no symptoms, increasing severity, even without symptoms, increases the load on the left ventricle. Over time this can result in ventricular dilatation and congestive heart failure.

Mitral valve disease is conventionally treated by open heart surgery; either by surgical repair, which is usually performed using an annuloplasty ring, or by surgical replacement with a valve prosthesis. In some cases, such as when the valve is too damaged, mitral valves may require replacement. Mitral valve replacement may be performed robotically or manually. Surgical valve replacement or repair is often a demanding operation as it requires cardiopulmonary bypass and it can expose patients, especially elderly ones, to many risks.

A large variety of percutaneous or transcutaneous medical procedures are currently being developed and/or practiced. For example, transcatheter procedures are known for replacement of aortic and pulmonary heart valves. These procedures, which are performed under local anesthesia in the cardiac catheterization lab, rather than by cardiac surgery, offer benefits to these patients. According to such approaches, the valve is inserted on a delivery device similar to a catheter or a sheath and then implanted in the desired location via access through a large blood vessel such as the femoral artery, for example. This involves making a very small perforation in the patient's skin, such as in the groin area, in order to access the femoral artery. This minimally invasive option is usually safer than open heart surgery, and recovery times are typically shorter.

SUMMARY OF EMBODIMENTS

In accordance with some applications of the present invention a docking element is used with prosthetic mitral valve apparatus for treating a subject with a diseased mitral valve. The docking element is configured to become anchored to the subject's mitral valve, and to thereby facilitate anchoring of the prosthetic mitral valve apparatus to the subject's mitral valve. An atrial component of the docking element includes a plurality of links that are hingedly coupled to one another. The atrial component is typically delivered to the subject's mitral valve, while disposed in a constrained configuration inside a delivery device, the plurality of links forming a straight elongate shape while disposed in the constrained configuration. Upon being released from the delivery device, the atrial component is typically configured to loop around at least a portion of the mitral valve, by the links flexing with respect to one another. A ventricular component of the docking element typically includes two or more anchors that are placed underneath leaflets of the mitral valve and coupled to the atrial component.

For some applications, a guidewire is inserted into a subject's body via an insertion location in a vein of the subject. The guidewire is advanced such that a distal end of the guidewire exits the subject's body via an exit location in an artery of the subject, by passing the guidewire, sequentially, through the subject's vena cava, right atrium, interatrial septum, left atrium, mitral valve, left ventricle, and aorta. A first component of a mitral valve implant (e.g., the ventricular component of the docking element) is advanced to a ventricular side of the subject's mitral valve, by advancing the first component over the guidewire from the exit location in the artery, and a second component of the mitral valve implant (e.g., the atrial component of the docking element) is advanced to an atrial side of the subject's mitral valve, by advancing the second component over the guidewire from the insertion location in the vein. The mitral valve implant is then anchored to the subject's mitral valve by coupling the first and second components to each other.

For some applications, a docking element includes a ring, and a frame extending from the ring. Typically, the docking element is deployed within the subject's left atrium, such that (a) no portion of the docking element extends through the subject's native mitral valve, (b) the ring is disposed at a mitral valve annulus of the subject, and (c) the frame extends from the subject's mitral valve annulus until at least 30 percent of the height of the left atrium, e.g., more than 50 percent of the height of the left atrium. For some applications, the height of the frame is more than 15 mm (e.g., more than 20 mm), and/or less than 40 mm (e.g., less than 35 mm), e.g., between 15 and 40 mm, or between 20 and 35 mm. As described in further detail below, typically, the docking element becomes anchored to the subject's heart by virtue of (a) outward radial force exerted by ring upon the mitral valve annulus, (b) outward radial force exerted by the frame upon the wall of left atrium, (c) tissue ingrowth from the mitral valve annulus to the ring (and/or components coupled thereto), and/or (d) tissue ingrowth from the inner wall of the left atrium to the frame (and/or components coupled thereto).

Typically, the docking element is implanted at the native mitral valve more than one week, or more than one month, before the implantation of the prosthetic mitral valve apparatus. Subsequent to the implantation of the docking element, and before the implantation of the prosthetic mitral valve apparatus, the anchoring of the docking element is typically strengthened by virtue of tissue ingrowth that occurs around the docking element. Typically, by virtue of the fact that no portion of the docking element extends through the subject's native mitral valve, the native mitral valve leaflets are able to continue functioning in their normal manner subsequent to the implantation of the docking element, and prior to the implantation of the prosthetic mitral valve apparatus. For some applications, the docking element itself has a therapeutic effect, by impeding progression of mitral annulus dilation.

The above-described, two-stage implantation procedure is somewhat analogous to a valve-in-valve procedure, whereby a new prosthetic valve is implanted inside a previously-implanted prosthetic valve. In such cases, the new valve typically becomes anchored within the previously-implanted valve, and the previously-implanted valve is strongly anchored to the native mitral valve, by virtue of tissue ingrowth with respect to the previously-implanted valve, as well as mechanical force exerted upon the heart by the previously-implanted prosthetic valve. Similarly, in accordance with some applications of the present invention, initially, the docking element is implanted and is allowed to become anchored to the subject's heart by virtue of tissue ingrowth with respect to the docking element, as well as mechanical force exerted upon the heart by the docking element. Subsequently, once the docking element is anchored within the subject's heart, prosthetic mitral valve apparatus is anchored to the docking element.

For some applications, a docking element includes a ring and a frame, as described hereinabove. For some applications, when the docking element is in a deployed state inside the left atrium, the ring is disposed transversely with respect to the frame, such that a plane defined by the ring is substantially parallel to the longitudinal axis of the frame. For some such applications, the docking element is placed into left atrium, via the interatrial septum, by advancing the docking element, along its longitudinal axis, in a lateral direction with respect to the subject's left atrium. Subsequently, without substantially rotating the docking element, the docking element is deployed within the subject's left atrium, such that the ring is disposed at the native mitral annulus, and is disposed transversely with respect to the frame. By virtue of the docking element deploying in this manner, the docking element does not need to be rotated with respect to the left atrium between being transseptally inserted into the left atrium, and being deployed within the left atrium. By contrast, if the ring was disposed at a longitudinal end of the frame such that the plane defined by the ring was substantially perpendicular to the longitudinal axis of the frame, it would be challenging to perform a transeptal insertion of the docking element. This is because the frame would need to be rotated and released from a delivery device within the relatively small volume that is defined by the left atrium.

There is therefore provided, in accordance with some applications of the present invention, apparatus for treating a subject with a diseased mitral valve, the apparatus including:

a docking element configured to be implanted within a left atrium of the subject such that no portion of the docking element extends through the subject's mitral valve, the docking element being configured to become anchored to tissue of the left atrium at least partially via ingrowth of the tissue of the left atrium to the docking element, the docking element including:

a ring configured to be implanted at a mitral valve annulus of the subject;

a frame extending upwardly from the ring, a height of the frame being at least 15 mm, the frame being configured to radially expand against an inner wall of the subject's left atrium; and a prosthetic mitral valve apparatus configured:
  subsequent to the ingrowth of the tissue of the left atrium to the docking element having occurred, to be placed at least partially inside the docking element, and
  to become anchored to the docking element, at least partially by radially expanding against the ring.

In some applications, the docking element further includes a left-atrial-appendage anchor configured to become anchored within a left atrial appendage of the subject.

In some applications, the frame includes a plurality of struts, and the ring is defined by at least some of the struts of the frame.

In some applications, a plane defined by the ring is parallel to the longitudinal axis of the frame.

In some applications, the frame of the docking element includes tissue-ingrowth elements coupled thereto, the tissue-ingrowth elements being configured to encourage tissue ingrowth with respect to the frame.

In some applications, the tissue-ingrowth elements include fabric sheets with fibers disposed thereon, the fibers being disposed substantially perpendicularly with respect to the fabric sheets.

In some applications, the apparatus further includes a fabric layer disposed upon the frame of the docking element.

In some applications, the fabric layer defines holes therethrough, the holes defined by the fabric layer being configured to be disposed in a vicinity of junctions of the left atrium with pulmonary veins of the subject, when the docking element is in an implanted state within the subject's left atrium.

In some applications:
  the docking element is configured to be placed into the subject's left atrium of the subject, via an interatrial septum of the subject, by advancing the docking element in a lateral direction with respect to the left atrium, along a longitudinal axis of the frame; and
  the ring is disposed laterally with respect to the frame, such that the ring is substantially parallel with the longitudinal axis of the frame.

In some applications, the docking element is configured to be deployed within the subject's left atrium, such that the longitudinal axis of the frame is substantially parallel to the subject's native mitral valve annulus.

There is further provided, in accordance with some applications of the present invention, a method for treating a subject with a diseased mitral valve, the method including:
  inserting a docking element into a left atrium of the subject, the docking element including a ring, and a frame extending from the ring;
  deploying the docking element within the subject's left atrium, such that (a) no portion of the docking element extends through the subject's mitral valve, (b) the ring is disposed at a mitral valve annulus of the subject, and (c) the frame extends from the subject's mitral valve annulus until at least a height of at least 15 mm from the mitral valve annulus;
  leaving the docking element within the subject's left atrium in the deployed state for a period of at least one week; and
  subsequent thereto,
    inserting a prosthetic mitral valve apparatus to inside the ring; and
    causing the prosthetic mitral valve apparatus to radially expand against the ring, such that the prosthetic mitral valve apparatus is anchored within the ring.

In some applications, deploying the docking element within the subject's left atrium includes deploying the docking element within the subject's left atrium, such that at least a portion of the docking element is disposed within a left atrial appendage of the subject.

In some applications, inserting the docking element includes inserting the docking element into the subject's left atrium transseptally in a direction that is parallel to a longitudinal axis of the frame, and deploying the docking element within the subject's left atrium includes deploying the docking element within the subject's left atrium such that a plane defined by the ring is substantially parallel to the longitudinal axis of the frame.

In some applications, inserting the docking element includes inserting the docking element into the subject's left atrium transseptally in a direction that is parallel to a longitudinal axis of the frame, and deploying the docking element within the subject's left atrium includes deploying the docking element within the subject's left atrium such that the longitudinal axis of the frame is substantially parallel to a plane defined by the subject's mitral valve annulus.

In some applications, deploying the docking element within the subject's left atrium includes deploying the docking element within the subject's left atrium such that the frame does not contact tissue of the left atrium in a vicinity of junctions of the left atrium with pulmonary veins of the subject.

In some applications, inserting the docking element includes inserting the docking element into the subject's left atrium transseptally in a direction that is parallel to a longitudinal axis of the frame, and deploying the docking element within the subject's left atrium includes deploying the docking element within the subject's left atrium such that the ring is disposed at the subject's mitral valve annulus, and such that a plane defined by the ring is substantially parallel to the longitudinal axis of the frame.

In some applications, inserting the docking element includes inserting the docking element into the subject's left atrium transseptally in a direction that is parallel to a longitudinal axis of the frame, and deploying the docking element within the subject's left atrium includes deploying the docking element such that the longitudinal axis of the frame is substantially parallel to a plane defined by the subject's mitral valve annulus.

In some applications, inserting the docking element includes inserting the docking element, the frame of the docking element having tissue-ingrowth elements coupled thereto, the tissue-ingrowth elements being configured to encourage tissue ingrowth with respect to the frame.

In some applications, inserting the docking element includes inserting the docking element, the tissue-ingrowth elements including fabric sheets with fibers disposed thereon, the fibers being disposed substantially perpendicularly with respect to the fabric sheets.

In some applications, inserting the docking element includes inserting the docking element, the frame of the docking element being covered with a fabric layer.

In some applications, inserting the docking element includes inserting the docking element, the fabric layer defining holes therethrough, and deploying the docking element within the subject's left atrium includes deploying the docking element within the subject's left atrium such that the holes defined by the fabric layer are disposed in a vicinity of junctions of the left atrium with pulmonary veins of the subject.

In some applications:
    inserting the docking element into the subject's left atrium includes inserting the docking element into the subject's left atrium, via an interatrial septum of the subject, by advancing the docking element in a lateral direction with respect to the subject's left atrium; and
    deploying the docking element within the subject's left atrium includes deploying the docking element within the subject's left atrium without substantially rotating the docking element subsequent to the advancement of the docking element.

In some applications, advancing the docking element in the lateral direction with respect to the left atrium includes advancing the docking element in a direction that is parallel to a longitudinal axis of a frame of the docking element, and deploying the docking element within the subject's left atrium includes deploying the docking element within the subject's left atrium such that a plane defined by the ring is disposed parallel to the longitudinal axis of the frame.

The present invention will be more fully understood from the following detailed description of embodiments thereof, taken together with the drawings, in which:

BRIEF DESCRIPTION OF THE DRAWINGS

FIG. 1 is a schematic illustration of a prosthetic mitral valve apparatus and a docking element configured to facilitate anchoring of the prosthetic mitral valve apparatus to a subject's mitral valve, in accordance with some applications of the present invention;

DETAILED DESCRIPTION OF EMBODIMENTS

Figure 2A:
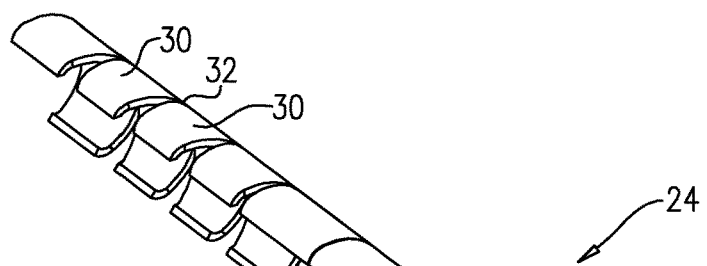
FIGS. 2A, 2B, and 2C are schematic illustrations of links of an atrial component of the docking element, in accordance with some applications of the present invention.

Reference is now made to FIG. 1, which is a schematic illustration of a prosthetic mitral valve apparatus 20 and a docking element 22 configured to facilitate anchoring of the prosthetic mitral valve apparatus to a subject's mitral valve. Typically, the prosthetic mitral valve apparatus is a stented valve that comprises a stented frame that is configured to support prosthetic valve leaflets 21. For example, the prosthetic mitral valve apparatus may be generally as described in WO 15/173794 to Spenser, which is incorporated herein by reference. The prosthetic mitral valve apparatus is typically implanted within the native mitral valve of a subject with a diseased native valve, and the prosthetic valve leaflets function such as to replace the functioning of the native valve leaflets. Typically, the prosthetic valve leaflets are configured to act as a one-way valve, whereby in their open positions with respect to one another the leaflets allow flow to pass through the prosthetic valve apparatus from the inlet (on the atrial side) to the outlet (on the ventricular side), whereas reverse flow is prevented due to collapsible slack portions of the valve leaflets collapsing inwardly to block the reverse flow.

For some applications, prior to implanting the prosthetic mitral valve apparatus, docking element 22 is implanted at the native mitral valve. Typically, the docking element includes a first, atrial component 24, configured to be placed on the atrial side of the mitral valve, and at least one second, ventricular component 26 configured to be placed on a ventricular side of the mitral valve. Further typically, the docking element includes two or more ventricular components 26. The docking element itself becomes anchored to the mitral valve by the atrial and ventricular components being coupled to one another, e.g., via coupling elements 28, such that tissue of the mitral valve, and/or tissue that surrounds the mitral valve, is disposed between the atrial and ventricular components.

For some applications, coupling elements 28 are coupled to ventricular components 26 prior to being inserted into the subject's body, and/or are integrally formed with the ventricular components. Coupling elements 28 are typically inserted into the left ventricle with ventricular components 26. Subsequent to being inserted into the left ventricle, the coupling elements are coupled to atrial component 24. For example, the coupling elements may include portions that snap into the atrial component (or vice versa), such as to become coupled to the atrial component. Alternatively or additionally, the coupling elements and the atrial component may include threaded portions that become threadedly coupled to each other. For some applications, coupling elements 28 are coupled to atrial component 24, prior to being inserted into the subject's body, and/or are integrally formed with the atrial component. Coupling elements 28 are inserted into the left atrium with atrial component 24. Subsequent to being inserted into the left atrium, the coupling elements are coupled to ventricular components 26. For example, the coupling elements may include portions that snap into the ventricular components (or vice versa), such as to become coupled to the ventricular components. Alternatively or additionally, the coupling elements and the ventricular components may include threaded portions that become threadedly coupled to each other.

For some applications, the atrial component and the ventricular components are coupled to each other via coupling elements 28, prior to being inserted into the subject's body. For such applications, the atrial component and ventricular components are inserted into the subject's heart, while coupled to one another, e.g., as described hereinbelow with reference to FIG. 7.

Typically, the docking element is implanted at the native mitral valve more than one week, or more than one month, before the implantation of the prosthetic mitral valve apparatus. Subsequent to the implantation of the docking element, and before the implantation of the prosthetic mitral valve apparatus, the anchoring of the docking element is typically strengthened by virtue of tissue ingrowth that occurs around the docking element. Typically, the docking element is implanted with respect to the native mitral valve, such that the native mitral valve leaflets are able to continue functioning in their normal manner subsequent to the implantation of the docking element, and prior to the implantation of the prosthetic mitral valve apparatus. For some applications, the docking element and the prosthetic mitral valve apparatus are implanted at the native mitral valve in the same procedure as each other, with the docking element typically being implanted prior to the prosthetic mitral valve apparatus.

Figure 2B:
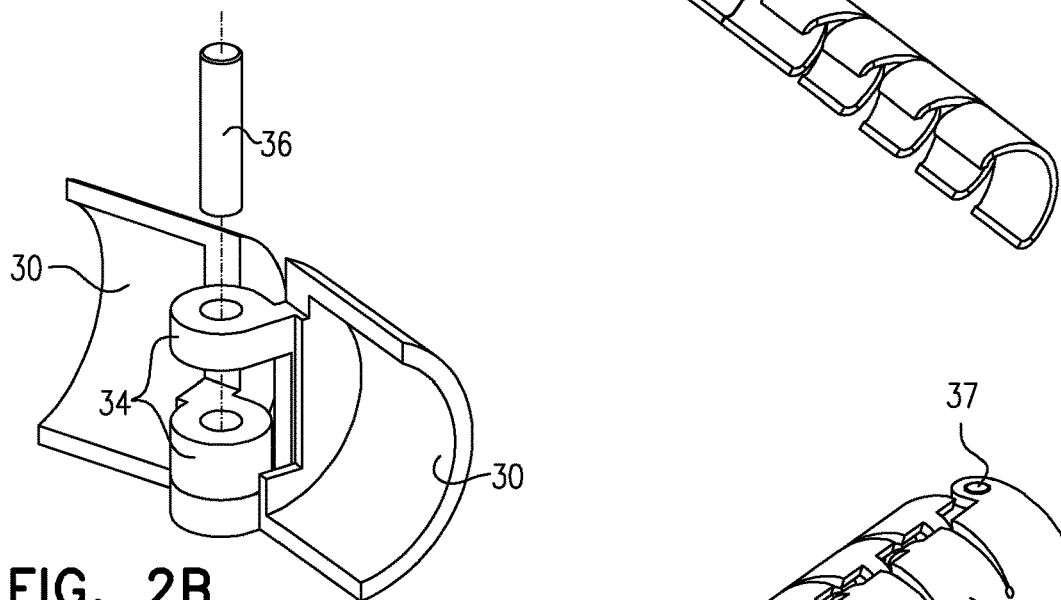
Figure 2C:
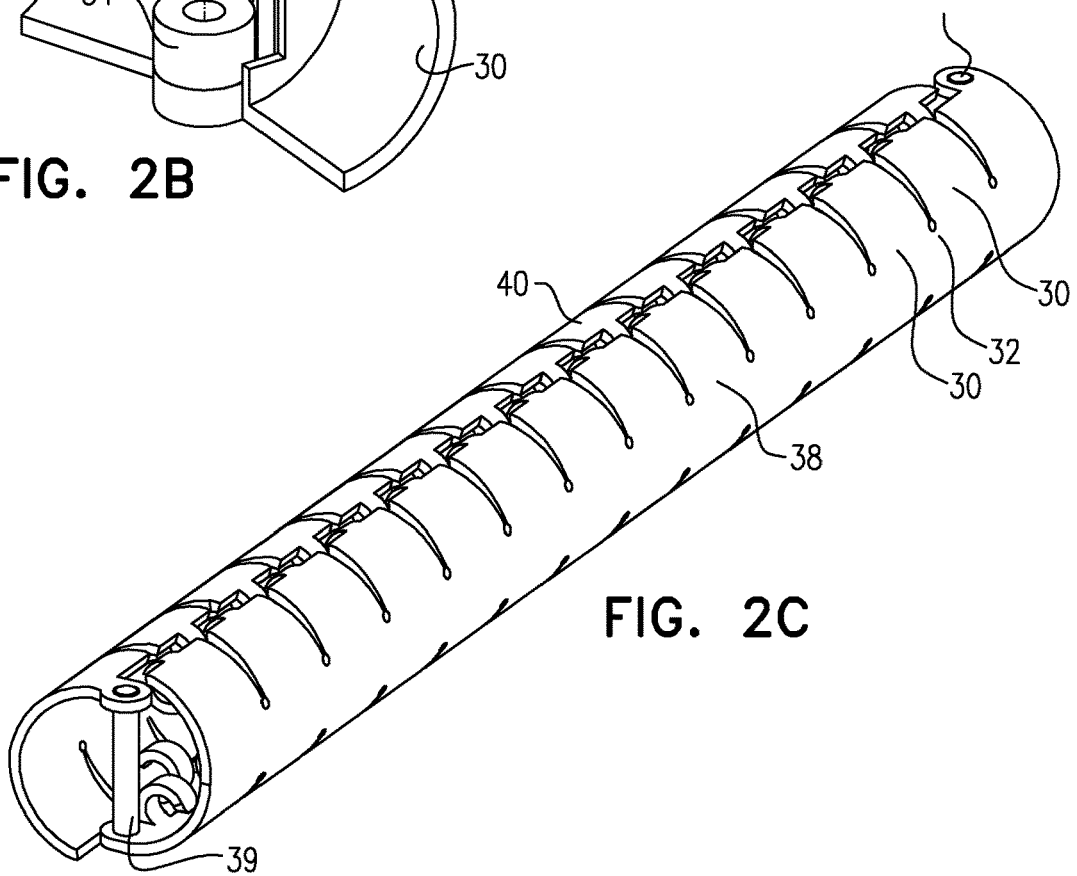

Reference is now made FIGS. 2A, 2B, and 2C, which are schematic illustrations of links 30 of atrial component 24 of the docking element 22, in accordance with some applications of the present invention. As described hereinabove, typically, the docking element includes atrial component 24, configured to be placed on the atrial side of the mitral valve, and at least one ventricular component 26 configured to be placed on a ventricular side of the mitral valve. For some applications, the atrial component includes a plurality of links, which are hingedly coupled to one another, as shown. For some applications, the links are coupled to each other by flexible connecting elements 32 (e.g., as shown in FIGS. 2A and 2C). For some applications, the links and the flexible connecting elements are cut from a single piece of a material (such as, a single piece of a metal, a single piece of a metal alloy (such as nitinol), or a single piece of plastic), and the flexible connecting elements constitute locations at which the material is thinner than at the links, or locations at which notches are cut into the edges of the material, such that the links flex with respect to one another around those locations. Alternatively or additionally, as shown in FIG. 2B, the links are hingedly coupled to one another via a hinge mechanism, such as cylinders 34 that are disposed around a pin 36, such that they pivot around the pin.

Figure 4:
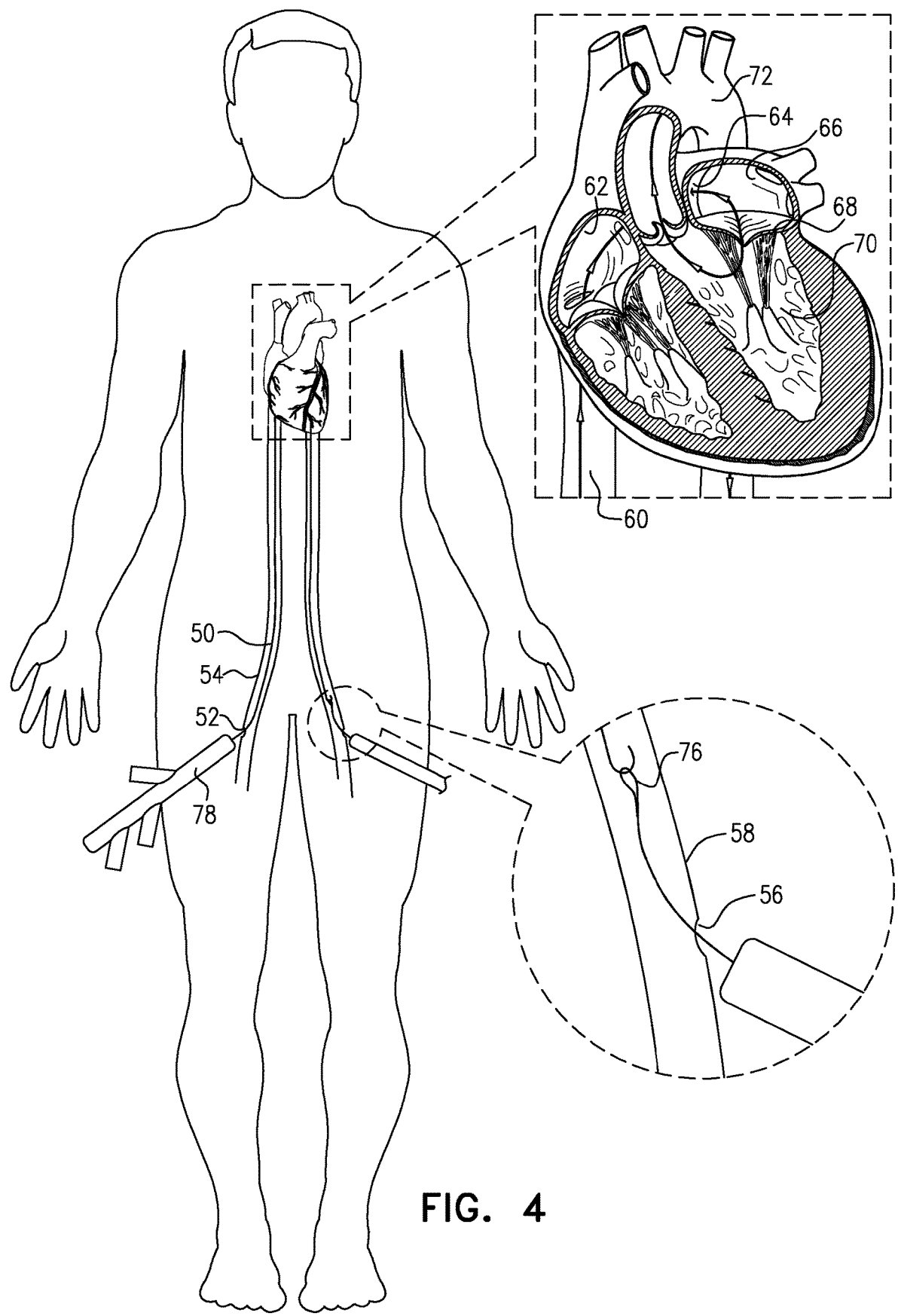
FIG. 4 is a schematic illustration of a guidewire that is inserted into the subject's body via an insertion location in a vein (e.g., the femoral vein), and which exits that subject's body via an exit location in an artery (e.g., the femoral artery), in accordance with some applications of the present invention.

Typically, atrial component 24 is configured to be delivered to the subject's mitral valve, while disposed in a constrained configuration inside a delivery device (e.g., delivery device 78, shown in FIG. 4). Further typically, the atrial component defines a straight elongate shape while disposed in the constrained configuration. For example, FIGS. 2A and 2C show the atrial component as configured while disposed inside a delivery device. FIGS. 2A and 2C show the atrial component in the absence of the delivery device, for illustrative purposes. Upon being released from the delivery device, the atrial component is configured to loop around at least a portion of the mitral valve (and for some applications, to loop around the full circumference of the mitral valve), by the links flexing with respect to one another. For some applications, the atrial component is shape set, such that, upon being released from the delivery device, the links flex with respect to one another automatically. Alternatively, the links are manually flexed with respect to one another such that the atrial component loops around at least a portion of the mitral valve. For some such applications, the ends of the atrial component are then coupled with respect to each other, e.g., using a cinching mechanism, and/or a connect-and-lock mechanism.

For some applications, during delivery of the atrial component to the subject's mitral valve, the set of links are pre-formed as a ring, but are folded about two hinges 37 and 39, such that respective portions 38 and 40 of the set of links are disposed alongside each other within the delivery device, e.g., as shown in FIG. 2C. Upon being released from the delivery device, the links form a ring by the centers of portions 38 and 40 moving away from each other, and the portions flexing about hinges 37 and 39.

Figure 3A:
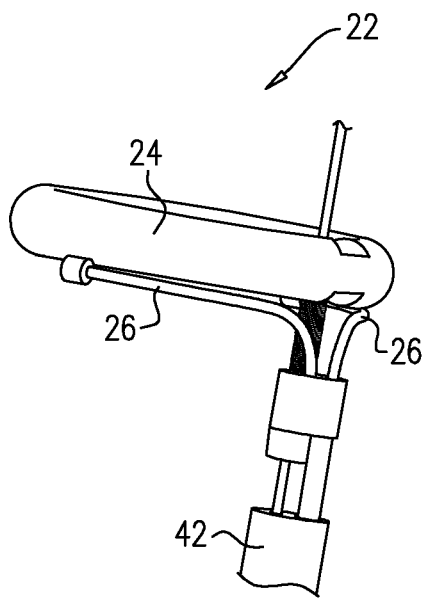
FIGS. 3A, 3B, and 3C are schematic illustrations of a ventricular component of the docking element, in accordance with some applications of the present invention.
Figure 3B:
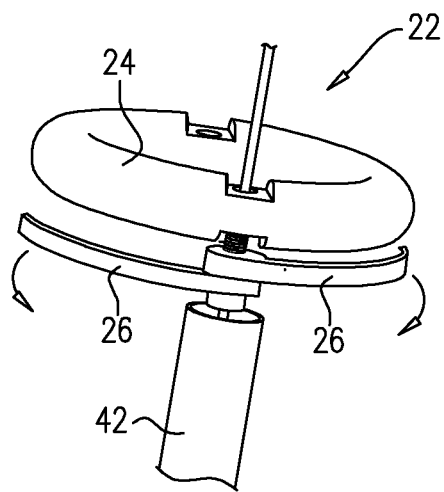
Figure 3C:
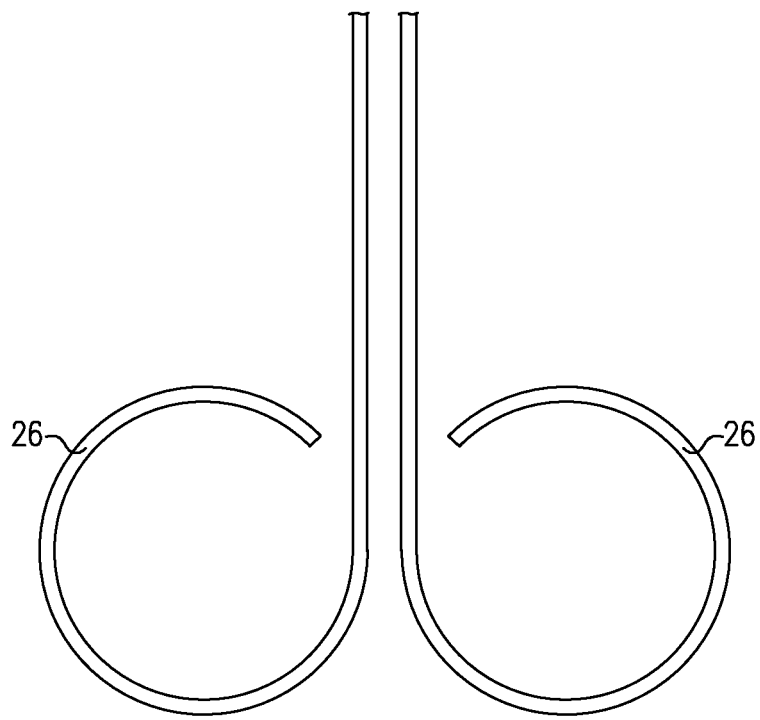

Reference is now made to FIGS. 3A, 3B, and 3C, which are schematic illustrations of ventricular components 26 of docking element 22, in accordance with some applications of the present invention. Typically, the ventricular components include one or more anchors that are placed underneath the leaflets of the mitral valve and are coupled to atrial component 24, as described hereinabove. For some applications, the ventricular components are coupled to the atrial component via a commissure of the mitral valve. Typically, for such applications, two ventricular components are used and respective ventricular components are coupled to the atrial component via respective mitral valve commissures. For some applications, one or more holes are created (e.g., via piercing, or ablation) in one or both of the mitral valve leaflets and the ventricular components are coupled to the atrial component via the holes in the valve leaflet(s). For some such applications, three or more ventricular components are used. In such applications, the operator typically does not need to align any component of the docking element with commissures of the native mitral valve.

For some applications, during insertion of the ventricular components 26 into the subject's left ventricle, the ventricular components are disposed inside a delivery device 42 in elongate configurations. Upon being released from the delivery device, the ventricular components are configured (e.g., automatically configured, due to shape setting of the ventricular components) to extend radially outwardly from the end of the delivery device, e.g., as shown in FIG. 3A. For some applications, the ventricular components are configured to curve such as to conform with the shape of the mitral valve annulus. For some applications, during insertion of the ventricular components into the subject's left ventricle, the ventricular components are wound into spirals, while disposed inside delivery device 42. Upon being released from the delivery device, the ventricular components are configured (e.g., automatically configured, due to shape setting of the ventricular components) to extend radially outwardly from the end of the delivery device, by the spirals unwinding, e.g., as shown in FIG. 3B. For some applications, as schematically illustrated in FIG. 3C, the ventricular components are configured to form circular shapes when disposed underneath the mitral valve leaflets, the circular shapes extending into the subject's left ventricle.

Reference is now made to FIG. 4, which is a schematic illustration of a guidewire 50 that is inserted into the subject's body via an insertion location 52 in a vein 54 (e.g., the femoral vein, as shown), and which exits that subject's body via an exit location 56 in an artery 58 (e.g., the femoral artery, as shown), in accordance with some applications of the present invention. For some applications, the guidewire is advanced through vein 54 into the subject's vena cava 60, and then, sequentially, through the vena cava into right atrium 62, through the interatrial septum 64, into left atrium 66, through mitral valve 68, through left ventricle 70, aorta 72, and then out of artery 58. For some applications, in order to pull the guidewire out of the artery 58, a snare 76 is used to grasp a distal portion of the guidewire.

For some applications, atrial component 24 of docking element 22 is advanced to the subject's left atrium by advancing the atrial component over the guidewire from insertion location 52 in vein 54 to the left atrium. Typically, a delivery device 78 (such as a catheter, as shown) is advanced over the guidewire from insertion location 52 in vein 54 to the left atrium, and the atrial component of the docking element is delivered to the left atrium over the guidewire and inside the delivery device. For some applications, ventricular component 26 is advanced to the subject's left ventricle by advancing the ventricular component over the guidewire, from exit location 56 in artery 58 to the left ventricle. For some applications, an additional delivery device (not shown) is advanced over the guidewire from exit location 56 in artery 58 to the left ventricle, and the ventricular component of the docking element is delivered to the left ventricle over the guidewire and inside the delivery device.

Figure 5:
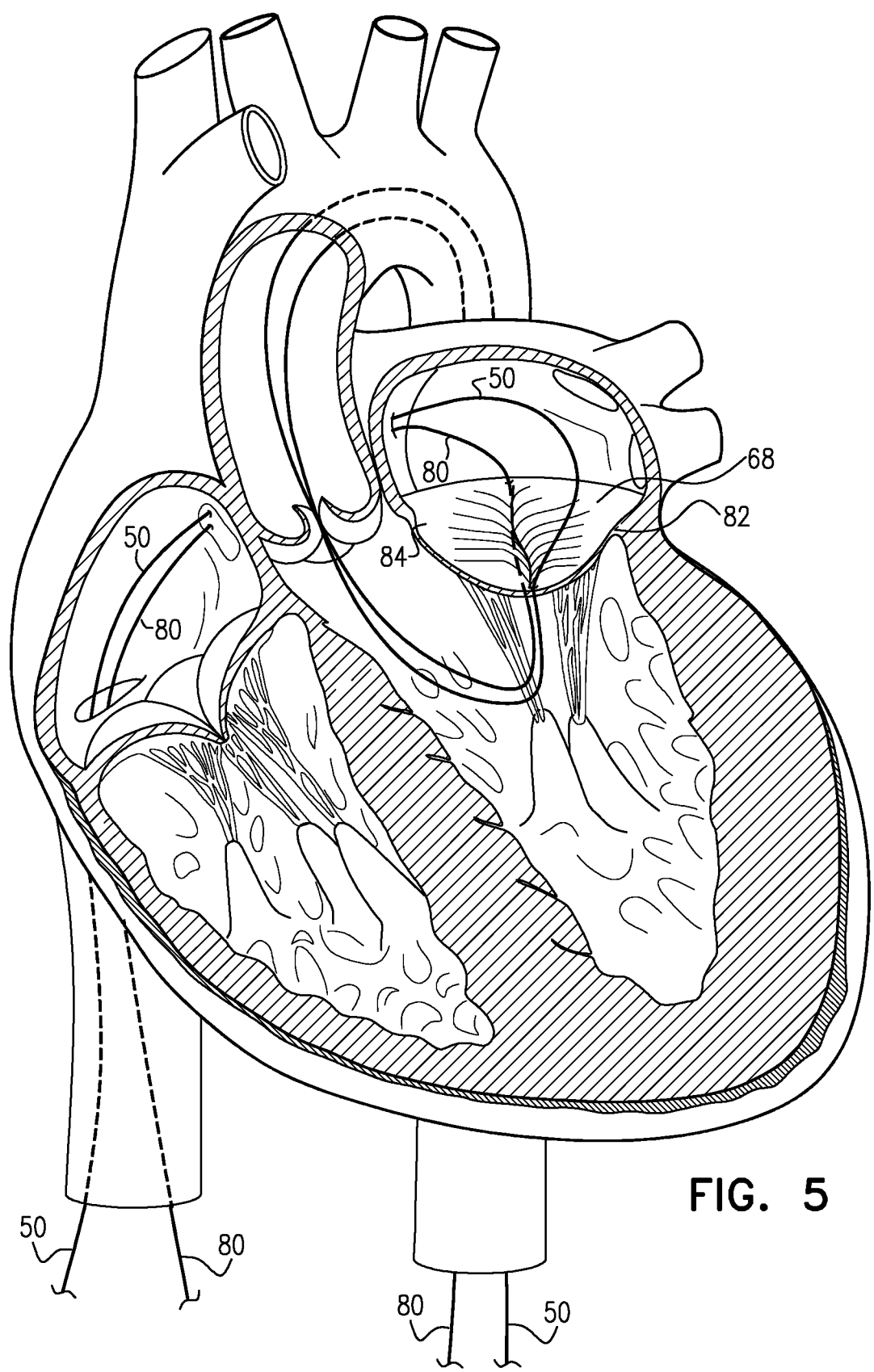
FIG. 5 is a schematic illustration of two guidewires that are advanced through a subject's body in the manner described with reference to FIG. 4, and which pass through respective commissures of the subject's mitral valve, in accordance with some applications of the present invention.
Figure 6:
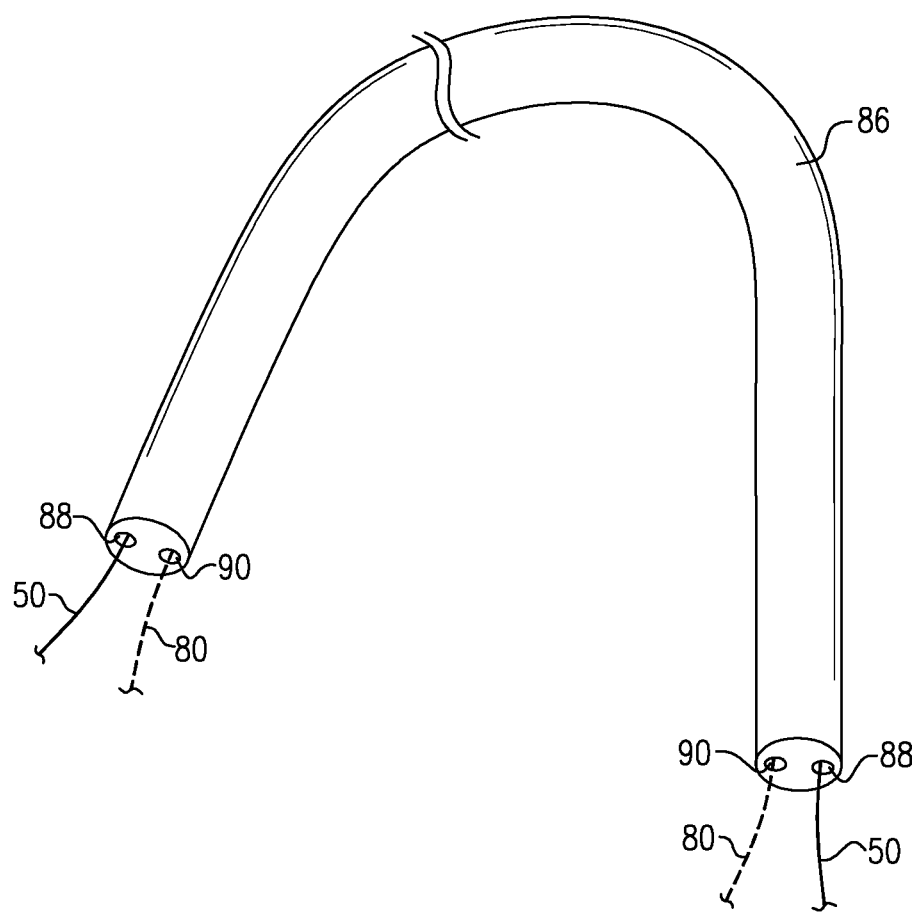
FIG. 6 is a schematic illustration of a catheter defining at least two channels therethrough, in order to facilitate the insertion of two guidewires through a subject's mitral valve, in accordance with some applications of the present invention.

Reference is now made to FIG. 5, which is a schematic illustration of two guidewires 50 and 80 that are advanced through a subject's body in the manner described with reference to FIG. 4, and which pass through respective commissures 82 and 84 of the subject's mitral valve 68, in accordance with some applications of the present invention. Reference is also made to FIG. 6, which is a schematic illustration of a catheter 86 defining at least two channels 88 and 90 therethrough, in order to facilitate the insertion of two guidewires through respective commissures 82 and 84 of the subject's mitral valve 68, in accordance with some applications of the present invention.

For some applications, first guidewire 50 is advanced in the general manner described hereinabove with reference to FIG. 4. That is to say that the guidewire is inserted via insertion location 52 in vein 54 and is then advanced such that a distal end of the guidewire exits the subject's body via exit location 56 in artery 58, by passing the guidewire, sequentially, through the subject's vena cava 60, right atrium 62, interatrial septum 64, left atrium 66, mitral valve 68, left ventricle 70, and aorta 72. Subsequently, first channel 88 of catheter 86 is advanced over first guidewire 50 from insertion location 52 in vein 54 to exit location 56 in artery 58. Subsequent to advancement of catheter 86 over first guidewire 50, the second guidewire is advanced through channel 90 of catheter 86 from insertion location 52 in vein 54 to exit location 56 in artery 58. In this manner, the two guidewires pass from insertion location 52 in vein 54 to exit location 56 in artery 58 in parallel to one another, but without becoming twisted with one another. For some applications, more than two guidewires are inserted in parallel with one another using the above-described techniques, mutatis mutandis.

For some applications, the proximal ends of guidewires 50 and 80 are inserted into respective locations within atrial component 24. The atrial component is then inserted via insertion location 52 in vein 54 (typically, via a delivery device, such as a catheter) and is guided by the guidewires to atrium 66. When the atrial component is within the atrium, guidewires 50 and 80 position the respective locations within the atrial component at predesignated positions with respect to the subject's mitral valve. For example, the guidewires may guide portions of the atrial component to which coupling elements 28 are coupled (or to which coupling elements 28 are configured to become coupled) to commissures of the mitral valve or to holes that have been created in the mitral valve leaflets.

For some applications, a first ventricular component 26 is advanced over a first one of the guidewires from exit location 56 in artery 58 to a first one of the commissures of the mitral valve, and a second ventricular component 26 is advanced over a second one of the guidewires from exit location 56 in artery 58 to a second one of the commissures of the mitral valve. The first and second ventricular components are then coupled to atrial component 24, as described hereinabove. Typically, the ventricular components are advanced to the ventricle while disposed inside a delivery device, and the atrial component is advanced to the left atrium while disposed inside a delivery device.

For some applications, the techniques described herein for advancing a first component of a mitral valve implant to a ventricular side of the subject's mitral valve, by advancing the first component over a guidewire from an exit location in an artery, and advancing a second component of the mitral valve implant to an atrial side of the subject's mitral valve, by advancing the second component over the guidewire from an insertion location in a vein, are applied to mitral valve implants other than docking element 22, mutatis mutandis.

Figure 7:
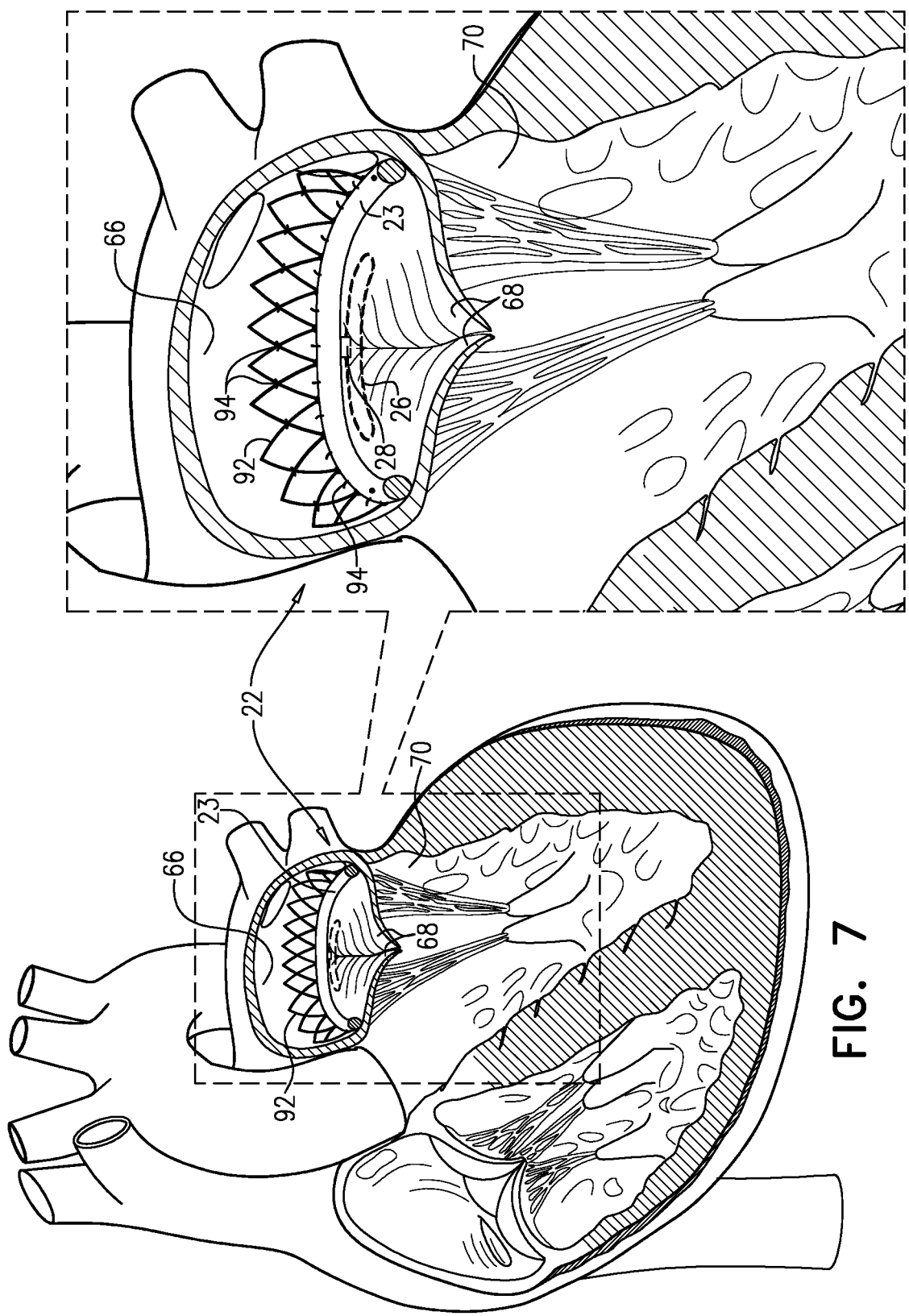
FIG. 7 is a schematic illustration of a docking element configured to facilitate anchoring of prosthetic mitral valve apparatus to a subject's mitral valve, in accordance with some applications of the present invention.

Reference is now made to FIG. 7, which is a schematic illustration of docking element 22, in accordance with some applications of the present invention. For some applications, atrial component 24 is coupled to a stabilizing frame 92, for example, by means of fabric (e.g., PET, PTFE, and/or nylon) and/or sutures. Typically, the stabilizing frame is a stent-like structure, the stabilizing frame comprising struts that define cells. For some applications, the stabilizing frame is at least partially flexible. Typically, the stabilizing frame is configured to expand such as to contact the walls of the atrium, and to thereby anchor the atrial component on the atrial side of the mitral valve annulus. For some such applications, the atrial component is a flexible ring made of fabric (e.g., PET, PTFE, and/or nylon) that is coupled to the stabilizing frame. For some applications, the stabilizing frame is covered with a material, such as PET, PTFE, and/or nylon. For some applications, the stabilizing frame is coupled to the tissue of the atrium, via tissue-coupling elements 94, such as, sutures or clips.

For some applications, as shown in FIG. 7, the ventricular components include substantially straight bars, and the bars are coupled to atrial component 24 via coupling elements 28 that are flexible (e.g., strings or wires). For some such applications, the ventricular components are inserted into the subject's left atrium via a delivery device, while coupled to the atrial component. Typically, the ventricular components are disposed within a lumen of the delivery device such that the longitudinal axes of the ventricular components are parallel to the longitudinal axis of the lumen. The ventricular components are passed into the subject's left ventricle (e.g., by being passed through commissures of the mitral valve, or by passed through holes that have been created within the mitral valve leaflets), while longitudinal axes of the ventricular components are parallel to the longitudinal axes of coupling elements 28. Subsequent to passing into the subject's left ventricle, the ventricular components rotate, such that longitudinal axes of the ventricular components are perpendicular to the longitudinal axes of coupling elements 28. The ventricular components are thereby prevented from passing back through the mitral valve and into the left atrium.

As described hereinabove, with reference to FIG. 1, typically, docking element 22 is configured to facilitate anchoring of prosthetic mitral valve apparatus 20 to the subject's mitral valve. For some applications, the docking element occupies some of the area defined by the native mitral valve annulus. Therefore, for some applications, prosthetic mitral valve apparatus is coupled to the subject's mitral valve, prosthetic valve leaflets 21 of the prosthetic mitral valve apparatus spanning a diameter that is less than the measured diameter of the native mitral valve annulus (the diameter of the native mitral valve annulus typically being measured using a mitral measuring ring, and/or using imaging methods, such as ultrasound). For example, the ratio of (a) the diameter that is spanned by the prosthetic valve leaflets to (b) the diameter of the native mitral valve annulus may be less than 5:6. Thus, for example, if the diameter of the native mitral valve annulus as measured by a mitral valve measuring ring is 30 mm, the diameter that is spanned by the prosthetic valve leaflets may be less than 25 mm. For some applications, one or more advantages of the prosthetic valve leaflets spanning a diameter that is less than that of the native mitral valve annulus, relative to using a prosthetic valve apparatus having prosthetic valve leaflets that span a greater diameter, may include: the prosthetic valve apparatus having a lower crimped profile, there being less foreign matter inside the subject's heart, lower forces being exerted on the prosthetic valve leaflets, better anchoring of the prosthetic valve apparatus, less interference with the native anatomy, and/or better preservation of a clear left ventricular outflow tract. Alternatively or additionally, prosthetic mitral valve apparatus having prosthetic valve leaflets spanning a diameter that is less than that of the native mitral valve annulus may be used for a different reason.

Typically, atrial component 24 and/or ventricular components 26 of docking element 22 are made from a super elastic, shape memory material such as nitinol alloy, which is shape set to define the shapes described hereinabove. Typically, in response to being released from a delivery device (e.g., delivery device 78, FIG. 4), the components automatically assume the above-described shapes. Alternatively or additionally, atrial component 24 and/or ventricular components 26 of docking element 22 are configured to undergo a phase change as they approach body temperature. For some applications, a polymer material is injected into a base material that forms the atrial component 24 and/or ventricular components 26 of docking element 22, the material being configured to impart desired stiffness, flexibility, resilience, or other properties.

Figure 8A:
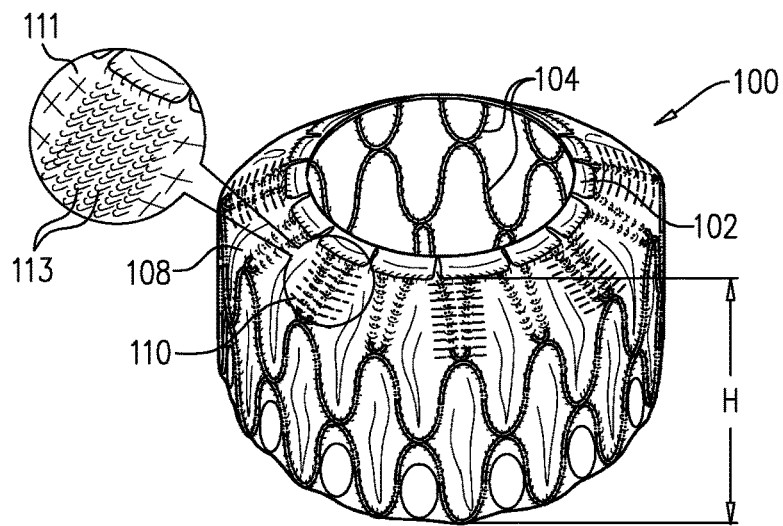
FIG. 8A is a schematic illustration of a docking element configured to facilitate anchoring of prosthetic mitral valve apparatus to a subject's mitral valve, in accordance with some alternative applications of the present invention.

Reference is now made to FIG. 8A, which is a schematic illustration of a docking element 100 configured to facilitate anchoring of prosthetic mitral valve apparatus to a subject's mitral valve, in accordance with some alternative applications of the present invention. Docking element 100 is generally similar to docking element 22 described hereinabove, except for the differences described hereinbelow. Typically, docking element 100 is configured to anchor prosthetic mitral valve apparatus 20 to native mitral valve 68, e.g. using generally similar techniques to those described hereinabove.

Figure 8B:
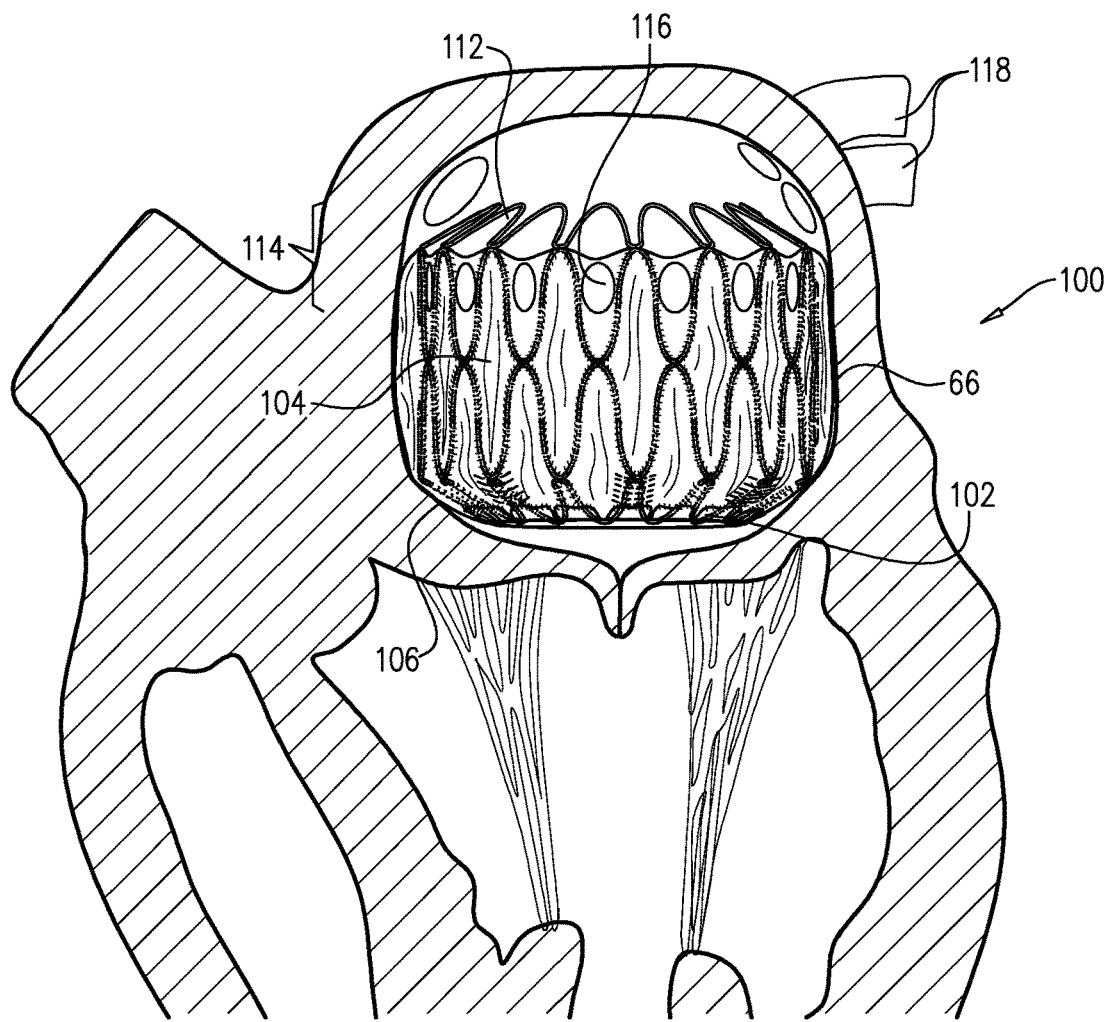
FIG. 8B is a schematic illustration of the docking element of FIG. 8A disposed, in its entirety, within a subject's left atrium, in accordance with some applications of the present invention.

Reference is also made to FIG. 8B, which is a schematic illustration of docking element 100 disposed, in its entirety, within a subject's left atrium, in accordance with some applications of the present invention. For some applications, docking element 100 includes a ring 102 and a frame 104 extending from the ring. Docking element 100 is typically deployed within the subject's left atrium 66, such that (a) no portion of the docking element extends through the subject's native mitral valve, (b) the ring is disposed at a mitral valve annulus 106 of the subject, and (c) the frame extends from the subject's mitral valve annulus until at least 30 percent of the height of the left atrium, e.g., more than 50 percent of the height of the left atrium. For some applications, a height H of the frame is at least 15 mm (e.g., at least 20 mm), and/or less than 40 mm (e.g., less than 35 mm), e.g., between 15 and 40 mm, or between 20 and 35 mm. Thus, when disposed inside the left atrium, the frame typically extends from the subject's mitral valve annulus until a height from the mitral valve annulus of at least 15 mm (e.g., at least 20 mm), and/or less than 40 mm (e.g., less than 35 mm), e.g., between 15 and 40 mm, or between 20 and 35 mm. As described in further detail below, typically, the docking element becomes anchored to the subject's heart by virtue of (a) outward radial force exerted by ring 102 upon mitral valve annulus 106, (b) outward radial force exerted by frame 104 upon the wall of left atrium 66, (c) tissue ingrowth from mitral valve annulus 106 to ring 102 (and/or components coupled thereto), and/or (d) tissue ingrowth from the inner wall of the left atrium to the frame (and/or components coupled thereto).

Typically, frame 104 of docking element is made of a super-elastic, shape-memory material, such as nitinol alloy. The frame is typically shape set to define a shape that conforms with the shape of the atrium, but that is oversized with respect to the left atrium, such that the frame is configured to exert an outward radial force against the inner wall of the left atrium. Typically, a fabric layer 108 is disposed around the outside of frame 104 and/or ring 102. For example, the fabric layer may be made of a fabric such as PET, PTFE, and/or nylon, and may be coupled to the outside of the frame and/or the ring using stitches. For some applications, the fabric of the fabric layer is configured to facilitate (a) tissue ingrowth to the frame, such that the frame becomes coupled to the inner wall of the left atrium, and/or (b) tissue ingrowth to the ring, such that the ring becomes coupled to the mitral valve annulus. Alternatively or additionally, tissue-ingrowth elements 110 are coupled to the fabric layer to encourage tissue ingrowth. For example, such tissue-ingrowth elements may include hooks or loops (e.g., similar to those used in hook-and-loop fasteners), barbs, clips, pins, etc. The tissue-ingrowth elements are configured to rub against the wall of the left atrium and to encourage tissue growth into the fabric of the fabric layer. For some applications, as shown, the tissue-ingrowth elements include fabric sheets 111, to which fibers 113 (e.g., hook shaped fibers, as shown) are coupled in a perpendicular arrangement with respect to the fabric sheets. For some applications, the fibers are coupled directly to fabric layer 108. The fibers are configured to rub against the wall of the left atrium and to encourage tissue growth into the fibers and the fabric sheets. Typically, the tissue-ingrowth elements are coupled to the fabric at a location that is configured to be disposed at or in a vicinity of (e.g., within 5 mm of) the mitral valve annulus. For some applications, the tissue-ingrowth elements define a 3D structure (e.g., as described hereinabove) that is configured to increase the contact area between the tissue and the frame and to serve as a scaffold for tissue to grow into.

Typically, docking element 100 is implanted at the native mitral valve more than one week, or more than one month, before the implantation of the prosthetic mitral valve apparatus. Subsequent to the implantation of the docking element, and before the implantation of the prosthetic mitral valve apparatus, the anchoring of the docking element is typically strengthened by virtue of tissue ingrowth that occurs around the docking element, e.g., as described hereinabove. Typically, by virtue of the fact that no portion of the docking element extends through the subject's native mitral valve, the native mitral valve leaflets are able to continue functioning in their normal manner subsequent to the implantation of the docking element, and prior to the implantation of the prosthetic mitral valve apparatus.

The above-described, two-stage implantation procedure is somewhat analogous to a valve-in-valve procedure, whereby a new prosthetic valve is implanted inside a previously-implanted prosthetic valve. In such cases, the new valve typically becomes anchored within the previously-implanted valve, and the previously-implanted valve is strongly anchored to the native mitral valve, by virtue of tissue ingrowth with respect to the previously-implanted valve, as well as mechanical force exerted upon the heart by the previously-implanted prosthetic valve. Similarly, in accordance with some applications of the present invention, initially, docking element 100 is implanted and is allowed to become anchored to the subject's heart by virtue of tissue ingrowth with respect to the docking element, as well as mechanical force exerted upon the heart by the docking element.

Subsequently, once the docking element is anchored within the subject's heart, prosthetic mitral valve apparatus is anchored to the docking element.

In accordance with respective applications of the present invention, docking element 100 and/or prosthetic mitral valve apparatus 20 is delivered to the subject's heart transapically, transseptally, and/or transaortically. For some applications, by delivering the docking element 100 and prosthetic mitral valve apparatus 20 in separate delivery steps, the size of the delivery device may be smaller than if the prosthetic mitral valve apparatus was to be delivered together with the docking element, ceteris paribus. For some applications, reducing the size of the delivery device that is required, in the above-described manner, facilitates transeptal insertion of the docking element and/or the prosthetic mitral valve apparatus.

Typically, the prosthetic mitral valve apparatus becomes anchored within ring 102 of docking element 100. Typically, the inner diameter of ring 102 is more than 20 mm. For some applications, the inner diameter of ring 102 is smaller than the inner diameter of native mitral valve annulus 106. For example, the inner diameter of ring 102 may be more than less than 30 mm, e.g., less than 28 mm. In this manner, the ring acts as an artificial mitral valve annulus that is smaller than the native mitral valve annulus. Typically, for such applications, the prosthetic mitral valve is configured to have a diameter that is less than the native mitral valve. For example, a ratio of the diameter of the prosthetic mitral valve to that of the native mitral valve may be less than 7:8, or less than 3:4. For some applications, using a prosthetic mitral valve that has a diameter that is less than the native mitral valve facilitates using a delivery device that is smaller than that which would be required by a prosthetic valve having the same diameter as the native mitral valve, ceteris paribus. For some applications, the prosthetic mitral valve has a diameter that is less than that of the native mitral valve, and has an effective orifice area of 1.8 cm^2 or more, which is typically sufficiently large for the heart to function healthily, in the majority of patients.

For some applications, the docking element and the prosthetic mitral valve apparatus are implanted above the native mitral valve in the same procedure as each other, with the docking element typically being implanted prior to the prosthetic mitral valve apparatus. For some such applications, when the prosthetic mitral valve apparatus is initially implanted, the prosthetic mitral valve leaflets are held open, for example, using sutures. Typically, the prosthetic mitral valve leaflets are maintained in the open state (e.g., using the sutures) for a period of more than more than one week, or more than one month, during which period the docking element becomes anchored to the subject's heart by virtue of tissue ingrowth, in accordance with the techniques described hereinabove. In this manner, during the period in which the docking element is becoming anchored to the subject's heart by virtue of tissue ingrowth, the docking element is not required to bear the load of blood impacting the prosthetic valve leaflets. Subsequently, the element that is keeping the prosthetic valve leaflets open (e.g., the sutures) is removed, such that the prosthetic valve leaflets begin functioning.

Referring again to FIG. 8B, frame 104 typically defines openings 112 at an upper portion 114 of the frame. Further typically, fabric layer 108 defines holes 116 therethrough at the upper portion of the frame. For some applications, opening 112 and holes 116 are configured to allow blood flow therethrough, such that blood flow from pulmonary veins 118 into the left atrium is not occluded.

Figure 9:
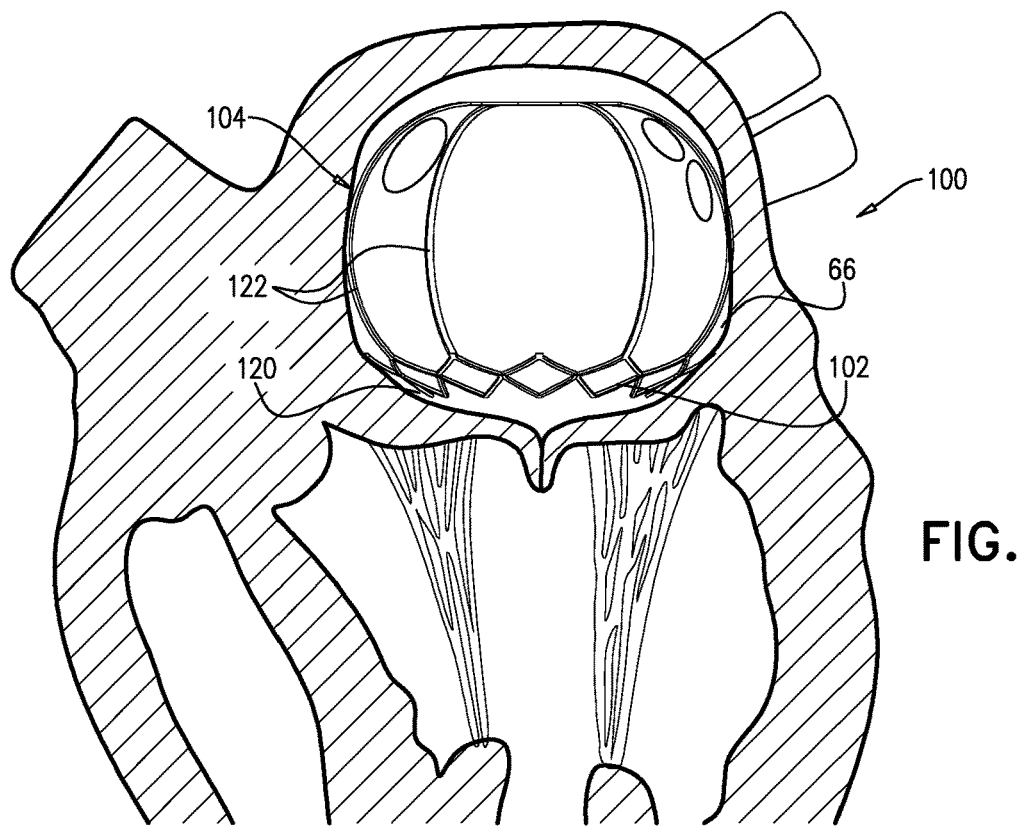
FIG. 9 is a schematic illustration of a docking element disposed, in its entirety, within a subject's left atrium, the docking element being configured to facilitate anchoring of prosthetic mitral valve apparatus to a subject's mitral valve, in accordance with some applications of the present invention.

Reference is now made to FIG. 9, which is a schematic illustration of docking element 100 disposed, in its entirety, within a subject's left atrium, the docking element being configured to facilitate anchoring of prosthetic mitral valve apparatus to a subject's mitral valve, in accordance with some applications of the present invention. Docking element 100 as shown in FIG. 9 is generally similar to docking element 100 as shown in FIGS. 8A and 8B, except for differences described hereinbelow. For some applications, as shown in FIGS. 8A and 8B, frame 104 of the docking element is shaped to define cells, which are distributed throughout the structure of the frame. For some applications, as shown in FIG. 9, frame 104 of the docking element is shaped to define a plurality of cells 120 that define ring 102. (It is noted that for such applications ring 102 is not necessarily shaped as a ring, but rather is a zig-zagged structure that comprises the edges of cells 120. In general, for some applications, the frame of the docking elements described herein includes struts and the ring of the docking element is defined by some of the struts of the frame.) The frame is configured to extend to the top portion of the left atrium via a plurality of elongate elements 122 that extend from cells 120. As described hereinabove, with reference to FIGS. 8A and 8B, typically, the structure of the frame is configured such that at junctions of the pulmonary veins with the left atrium (or in a vicinity of such junctions (e.g., within 2 mm of such junctions), the frame does not contact tissue of the heart, such that blood flow from the pulmonary veins into the left atrium is not occluded. For some applications (not shown), docking element as shown in FIG. 9 is covered with a fabric layer, and/or tissue ingrowth elements, which are typically generally as described hereinabove with reference to FIGS. 8A and 8B, mutatis mutandis.

Figure 10:
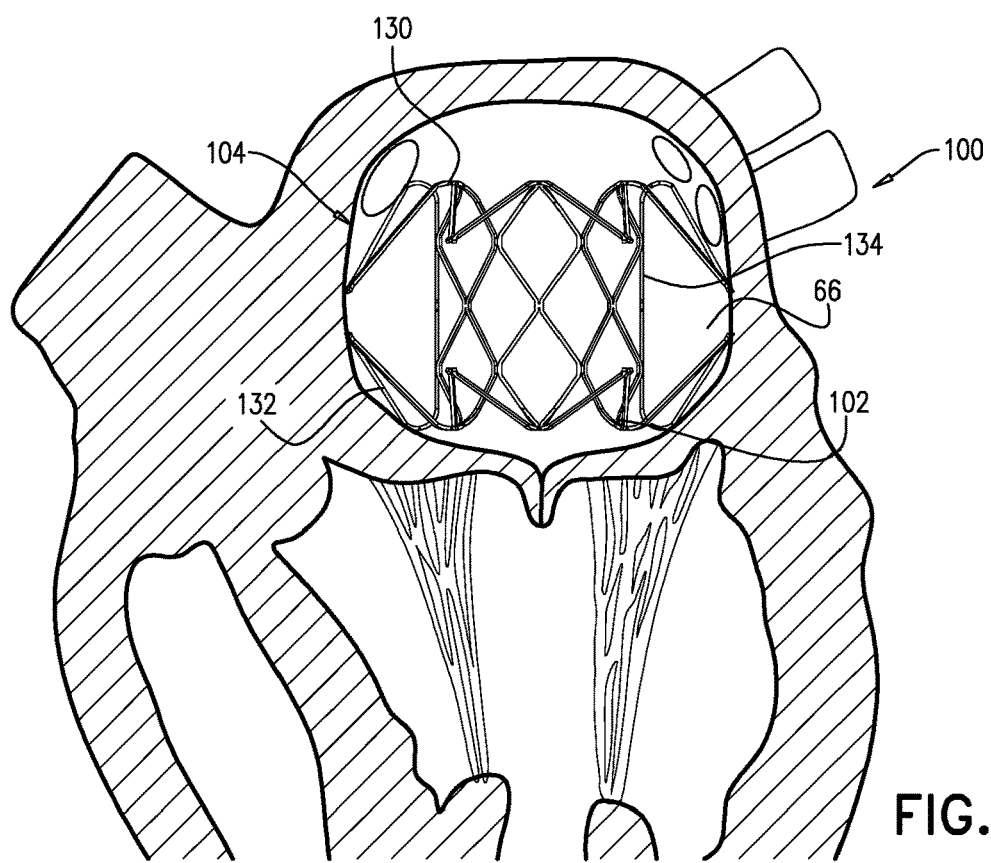
FIG. 10 is a schematic illustration of a docking element disposed, in its entirety, within a subject's left atrium, the docking element being configured to facilitate anchoring of prosthetic mitral valve apparatus to a subject's mitral valve, in accordance with some applications of the present invention.

Reference is now made to FIG. 10, which is a schematic illustration of docking element 100 disposed, in its entirety, within a subject's left atrium, the docking element being configured to facilitate anchoring of prosthetic mitral valve apparatus to a subject's mitral valve, in accordance with some applications of the present invention. Docking element 100 as shown in FIG. 10 is generally similar to docking element 100 as shown in FIGS. 8A and 8B, except for differences described hereinbelow. For some applications, as shown in FIGS. 8A and 8B, frame 104 of the docking element is configured to radially expand against the walls of the left atrium along the length of the frame. For some applications, as shown in FIG. 10, frame 104 of the docking element is shaped to define an upper portion 130, a lower portion 132, and an intermediate portion 134 disposed between the upper and lower portions. The upper and lower portions are configured to expand against the inner wall of the left atrium. For some applications lower portion 132 defines ring 102, which is configured to exert a radial force upon the mitral valve annulus. (It is noted that for such applications ring 102 is not necessarily shaped as a ring, but rather is a zig-zagged structure that comprises the edges of cells lower portion 132. In general, for some applications, the frame of the docking elements described herein includes struts and the ring of the docking element is defined by some of the struts of the frame.) The intermediate portion is configured to be narrower than the upper and lower portions, and not to contact the inner wall of the left atrium. For some applications, as shown, the upper and lower portions are inverted with respect to the intermediate portion. As described hereinabove, with reference to FIGS. 8A and 8B, typically, the structure of the frame is configured such that at junctions of the pulmonary veins with the left atrium (or in a vicinity of such junctions (e.g., within 2 mm of such junctions), the frame does not contact tissue of the heart, such that blood flow from the pulmonary veins into the left atrium is not occluded. For some applications (not shown), docking element as shown in FIG. 10 is covered with a fabric layer, and/or tissue ingrowth elements, which are typically generally as described hereinabove with reference to FIGS. 8A and 8B, mutatis mutandis. For some applications, only the upper and lower portions of the frame are covered with the fabric layer, and/or tissue ingrowth elements, and the intermediate portion is uncovered.

For some applications, the frame is configured to only apply a relatively low pressure to the inner wall of the left atrium, such that the frame conforms to the shape of the left atrium, rather than forcing the atrium to deform. For example, in the configurations shown in FIGS. 9 and 10, the frame may be configured to apply a relatively low pressure to the inner wall of the left atrium, such that the frame conforms to the shape of the left atrium, rather than forcing the atrium to deform. For some applications, in this manner, the frame allows the natural compliance of the inner wall of the left atrium to be substantially maintained. For some applications, frame 104 as shown in FIGS. 9 and 10 is able to be radially constrained (during insertion of the frame to the heart) to a smaller diameter than a frame as shown in FIGS. 8A and 8B, since the frame comprises less of the shape-memory material than the configuration shown in FIGS. 8A and 8B, mutatis mutandis.

Figure 11A:
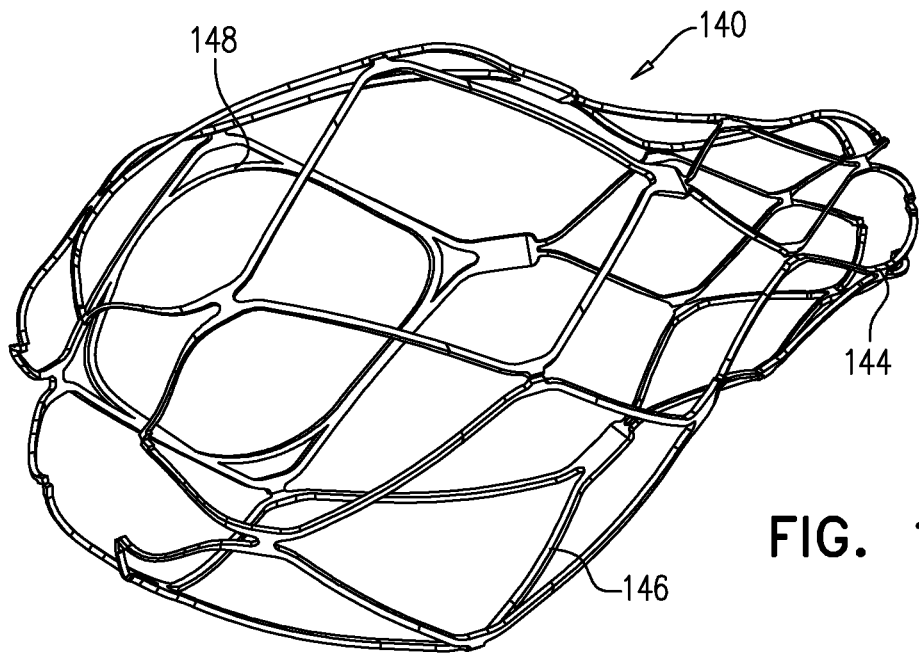
FIG. 11A is a schematic illustration of a docking element configured to facilitate anchoring of prosthetic mitral valve apparatus to a subject's mitral valve by a portion of the docking element becoming anchored to a left atrial appendage of the subject, in accordance with some alternative applications of the present invention.
Figure 11B:
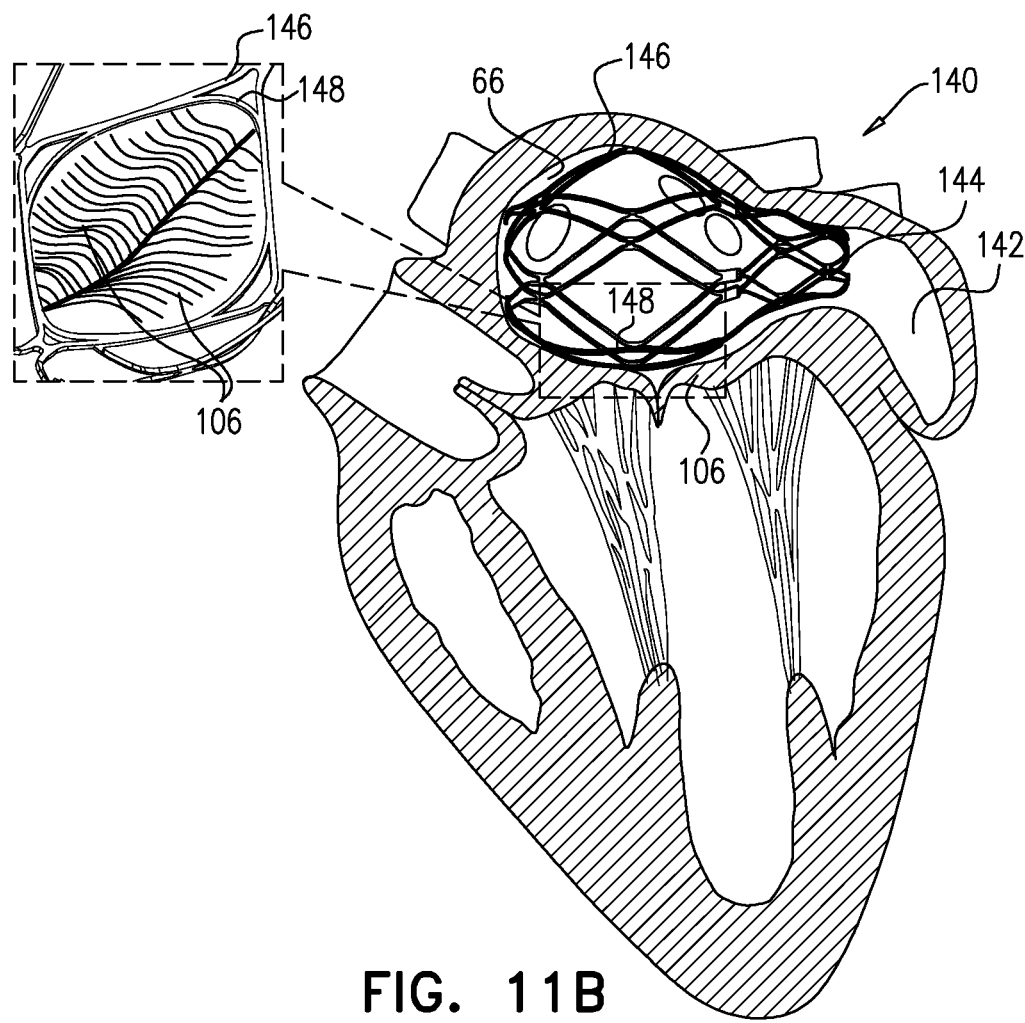
FIG. 11B is a schematic illustration of the docking element of FIG. 11A disposed, in its entirety, within a subject's left atrium with a portion of the docking element being anchored to a left atrial appendage of the subject, in accordance with some applications of the present invention.

Reference is now made to FIG. 11A, which is a schematic illustration of a docking element 140 configured to facilitate anchoring of prosthetic mitral valve apparatus to a subject's mitral valve by a portion of the docking element becoming anchored to a left atrial appendage 142 of the subject, in accordance with some alternative applications of the present invention. Reference is also made to FIG. 11B, which is a schematic illustration of docking element 140 disposed, in its entirety, within subject's left atrium with a left-atrial-appendage anchor 144 of the docking element being anchored to left atrial appendage 142, in accordance with some applications of the present invention. It is noted that, in general, in the context of the present application, including the claims, the description of an element as being disposed within the left atrium "in its entirety," should not be interpreted to exclude a portion of the element being disposed within the left atrial appendage.

For some applications, docking element 140 includes a frame 146, a ring 148, and left-atrial-appendage anchor 144. For some applications, as shown, ring 148 is defined by struts of frame 146. For some applications, the struts that define the ring are thicker than other struts of the frame. For some applications, the prosthetic mitral valve apparatus is configured to become coupled to the docking element, by the prosthetic mitral valve apparatus radially expanding against ring 148. As such, ring 148 typically bears much of the load of the forces that are exerted upon the prosthetic mitral valve apparatus. For some applications, the ring is configured to bear this load at least partially by virtue of the struts that define the ring being thicker than other struts of the frame.

Typically, in its deployed state inside the left atrium, the ring is disposed transversely with respect to the frame, such that a plane defined by the ring is substantially parallel to the longitudinal axis of the frame. For some applications, the docking element is placed into left atrium 66, via interatrial septum 64 (shown in FIG. 4), by advancing the docking element, along its longitudinal axis, in a lateral direction with respect to the subject's left atrium. Subsequently, without rotating the docking element, the docking element is deployed within the subject's left atrium, such that ring 148 is disposed at the native mitral annulus, and is disposed transversely with respect to the frame. Thus, even in the deployed state of the docking element, the longitudinal axis of the frame is substantially parallel to a plane defined by the subject's mitral valve annulus. By virtue of the docking element deploying in this manner, the docking element does not need to be substantially rotated with respect to the left atrium between being transseptally inserted into the left atrium, and being deployed within the left atrium. By contrast, if the ring was disposed at a longitudinal end of the frame such that the plane defined by the ring was substantially perpendicular to the longitudinal axis of the frame, this would make it challenging to insert the docking element transseptally. This is because the frame would need to be rotated (approximately 90 degrees relative to the interatrial septum) and released from the delivery device within the relatively small volume that is defined by the left atrium.

For some applications (not shown), docking element 140 is covered with a fabric layer, and/or tissue ingrowth elements, which are typically generally as described hereinabove with reference to FIGS. 8A and 8B, mutatis mutandis. As described hereinabove with reference to docking element 100 of FIGS. 8A and 8B, typically, docking element 140 becomes anchored to the subject's heart by virtue of (a) outward radial force exerted by ring 148 upon mitral valve annulus 106, (b) outward radial force exerted by frame 146 upon the wall of left atrium 66, (c) tissue ingrowth from mitral valve annulus 106 to ring 148 (and/or components coupled thereto), and/or (d) tissue ingrowth from the left atrium wall to the frame (and/or components coupled thereto). For some applications, docking element 140 additionally includes left-atrial-appendage anchor 144 which is configured to be inserted into the left atrial appendage, and to become anchored within the left atrial appendage, such as to further anchor the docking element with respect to the subject's heart.

It is noted that, for illustrative purposes, left atrial appendage 142 is shown in FIG. 11B as being to the right of the left atrium, when looking at the page, and frame 146 is shown as being disposed such that the longitudinal axis of the frame goes from the left to the right of the page. In a typical human heart, the left atrial appendage would come at least partially out of the page. Similarly, the longitudinal axis of the frame would extend at least partially in the direction from behind the page to in front of the page.

It is noted that, although FIGS. 11A and 11B show docking element 140 as including (a) left-atrial-appendage anchor 144, and (b) ring 148 that is disposed transversely with respect to the frame, the scope of the present invention includes a docking element that includes one of components (a) and (b), even in the absence of the other component. It is further noted that features of docking element 100 described hereinabove with reference to FIGS. 8A and 8B may be combined with features of docking element 140, described with reference to FIGS. 11A and 11B. For example, the height of frame 146 of docking element 140 may be at least 15 mm (e.g., at least 20 mm), and/or less than 40 mm (e.g., less than 35 mm), e.g., between 15 and 40 mm, or between 20 and 35 mm. Thus, when disposed inside the left atrium, the frame typically extends from the subject's mitral valve annulus until a height from the mitral valve annulus of at least 15 mm (e.g., at least 20 mm), and/or less than 40 mm (e.g., less than 35 mm), e.g., between 15 and 40 mm, or between 20 and 35 mm. As described hereinabove, with reference to FIGS. 8A and 8B, typically, the structure of frame 146 is configured such that, at junctions of the pulmonary veins with the left atrium (and/or in a vicinity of such junctions (e.g., within 2 mm of such junctions), the frame does not contact tissue of the heart (e.g., because the cells are open and are not covered with fabric, such that blood can flow through the cells). In this manner, blood flow from the pulmonary veins into the left atrium is not occluded.

Figure 12A:
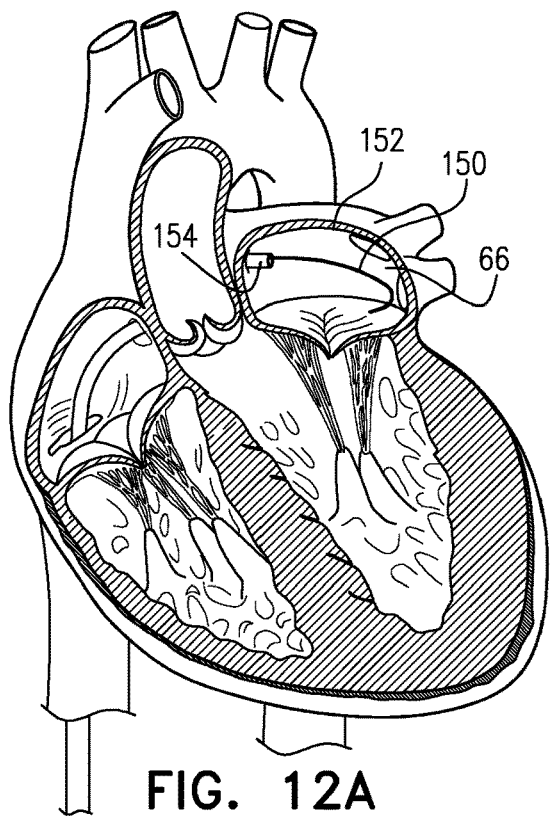
FIGS. 12A, 12B, and 12C are schematic illustration of respective steps of the implantation of a docking element that is configured to define a spiral that extends from a mitral annulus of the subject until a roof of the subject's left atrium, and to become anchored within the left atrium by exerting an outward radial force upon a wall of the subject's left atrium, in accordance with some applications of the present invention.
Figure 12B:
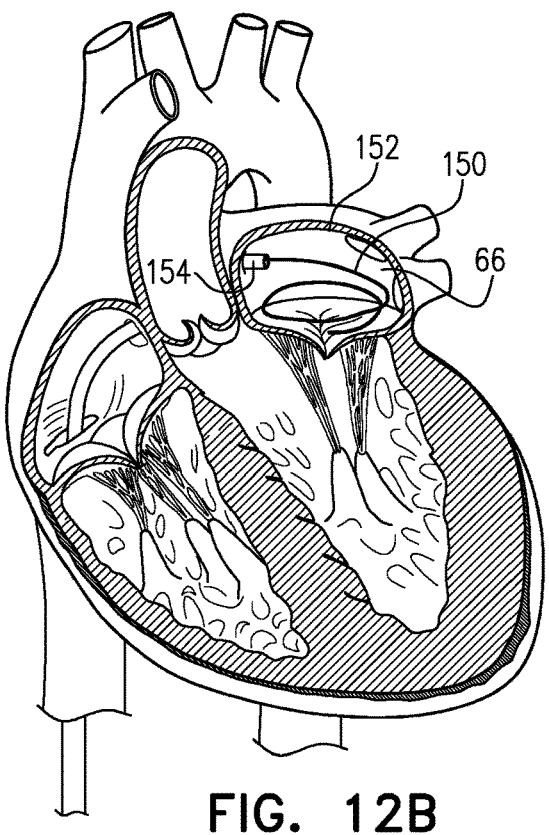
Figure 12C:
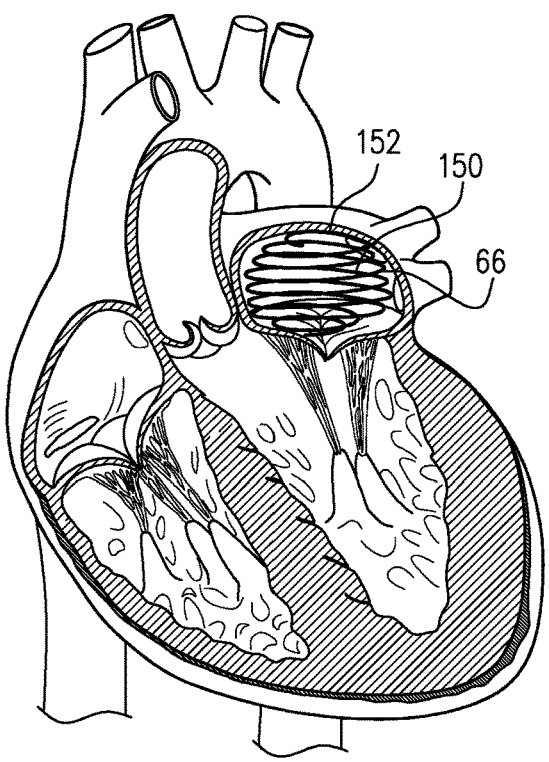

Reference is now made to FIGS. 12A, 12B, and 12C, which are schematic illustrations of respective steps of the implantation of a docking element 150 that is configured to define a spiral that extends from the mitral annulus until a roof 152 of the subject's left atrium 66, and becomes anchored within the left atrium by exerting an outward radial force upon the inner wall of the subject's left atrium, in accordance with some applications of the present invention. Typically, docking element 150 is configured to anchor prosthetic mitral valve apparatus 20 above the native mitral valve 68, e.g. using generally similar techniques to those described hereinabove.

Docking element 150 is typically made of a super-elastic, shape-memory material (e.g., a shape-memory alloy, such as nitinol), which is shape set to define a spiral shape that conforms with a shape of the left atrium, but that is oversized with respect to the left atrium, such that the spiral is configured to exert an outward radial force against the inner wall of the left atrium. For some applications, during insertion into the left atrium, the docking element is disposed in an elongate configuration inside a delivery device 154. For some applications, the delivery device is inserted into the left atrium transseptally, as shown in FIGS. 12A-C. Alternatively, the delivery device is inserted into the left atrium via a different route, e.g., transapically, or transaortically. Typically, once the distal end of the delivery device is disposed inside the left atrium, the docking element is advanced with respect to the delivery device. Further typically, the advancement of the docking element causes the docking element to assume a spiral shape, as shown in the transition from FIG. 12A to FIG. 12B, and from FIG. 12B to FIG. 12C.

For some applications, the apparatus and methods described herein are performed with respect to a tricuspid valve, and/or a different valve in a subject's body, mutatis mutandis.

There is therefore provided, in accordance with some applications of the present invention, the following inventive concepts:

Inventive concept 1. A method for treating a subject with a diseased mitral valve, the method comprising:
  inserting at least one guidewire into a body of a subject via an insertion location in a vein of a subject;
  advancing the at least one guidewire such that a distal end of the guidewire exits the subject's body via an exit location in an artery of the subject, by passing the guidewire, sequentially, through a vena cava of the subject, a right atrium of the subject, an interatrial septum of the subject, a left atrium of the subject, the mitral valve, a left ventricle of the subject, and an aorta of the subject;
  advancing a first component of a mitral valve implant to a ventricular side of the subject's mitral valve, by advancing the first component over the guidewire from the exit location in the artery;
  advancing a second component of the mitral valve implant to an atrial side of the subject's mitral valve, by advancing the second component over the guidewire from the insertion location in the vein; and
  anchoring the mitral valve implant to the subject's mitral valve by coupling the first and second components to each other.

Inventive concept 2. The method according to inventive concept 1, wherein:
  advancing the first component of the mitral valve implant to the ventricular side of the subject's mitral valve comprises advancing a ventricular component of a docking element to the ventricular side of the subject's mitral valve;
  advancing the second component of the mitral valve implant to the atrial side of the subject's mitral valve comprises advancing an atrial component of the docking element to the atrial side of the subject's mitral valve; and
  anchoring the mitral valve implant to the subject's mitral valve by coupling the first and second components to each other, comprises anchoring the docking element to the subject's mitral valve, to thereby facilitate anchoring of a prosthetic mitral valve apparatus to the subject's mitral valve Inventive concept 3. The method according to inventive concept 1 or inventive concept 2, wherein:
inserting at least one guidewire into the subject's body subject via the insertion location in the subject's vein comprises inserting two or more guidewires into the subject's body subject via the insertion location in the subject's vein;
advancing the at least one guidewire such that the distal end of the guidewire exits the subject's body via the exit location in the subject's artery comprises advancing the two or more guidewires such that distal ends of the two or more guidewires exit the subject's body via the exit location in the subject's artery; and
advancing the first component of the mitral valve implant to the ventricular side of the subject's mitral valve by advancing the first component over the guidewire from the exit location in the artery comprises advancing two or more first components of the mitral valve implant to the ventricular side of the subject's mitral valve, by advancing the first components over respective guidewires of the two or more guidewires from the exit location in the artery.

Inventive concept 4. The method according to inventive concept 3, wherein advancing the two or more guidewires such that distal ends of the two or more guidewires exit the subject's body via the exit location in the subject's artery comprises advancing the two or more guidewires via respective lumens of a catheter.

Inventive concept 5. The method according to inventive concept 3, wherein advancing the second component of the mitral valve implant to the atrial side of the subject's mitral valve by advancing the second component over the guidewire from the insertion location in the vein comprises using respective guidewires to position respective locations within the second component at predesignated positions with respect to the subject's mitral valve.

Inventive concept 6. Apparatus for treating a subject with a diseased mitral valve, comprising:
a mitral valve implant comprising:
a left atrial component configured to be inserted into a left atrium of the subject via a vena cava of the subject; and
a left ventricular component configured to be inserted into a left ventricle of the subject via an aorta of the subject,
the left atrial component and left ventricular component being configured to become anchored to the mitral valve by being coupled to one another.

Inventive concept 7. The apparatus according to inventive concept 6, wherein the apparatus is for use with a prosthetic mitral valve apparatus, and the mitral valve implant comprises a docking element configured to become anchored to the subject's mitral valve, and to thereby facilitate anchoring of the prosthetic mitral valve apparatus to the subject's mitral valve.

Inventive concept 8. The apparatus according to inventive concept 6 or inventive concept 7,
further comprising at least one guidewire configured to be advanced, from an insertion location in a vein of a subject to an exit location in an artery of the subject, by passing sequentially, through a vena cava of the subject, a right atrium of the subject, an interatrial septum of the subject, a left atrium of the subject, the mitral valve, a left ventricle of the subject, and an aorta of the subject,
wherein the left atrial component is configured to be inserted into the subject's left atrium by being advanced over the guidewire from the insertion location in the subject's vein, and the left ventricular component is configured to be advanced to the left ventricle by being advanced from the exit location in the subject's artery.

Inventive concept 9. The apparatus according to inventive concept 8, wherein:
the at least one guidewire comprises two or more guidewires configured to be advanced, in parallel to one another, from the insertion location in the subject's vein to the exit location in the subject's artery; and
the left ventricular component comprises two or more left ventricular components configured to be advanced to the left ventricle by being advanced from the exit location in the artery over respective guidewires of the two or more guidewires.

Inventive concept 10. The apparatus according to inventive concept 9, further comprising a catheter that defines two or more lumens that are parallel to one another, wherein the two or more guidewires are configured to be advanced, in parallel with one another, via respective lumens of the catheter.

Inventive concept 11. The apparatus according to inventive concept 9, wherein the guidewires are configured to position respective locations within the left atrial component at predesignated positions with respect to the subject's mitral valve.

Inventive concept 12. Apparatus for use with prosthetic mitral valve apparatus for treating a subject with a diseased mitral valve, the apparatus comprising:
a delivery device; and
a docking element configured to become anchored to the subject's mitral valve, and to thereby facilitate anchoring of the prosthetic mitral valve apparatus to the subject's mitral valve, the docking element comprising:
an atrial component that comprises a plurality of links that are hingedly coupled to one another, the atrial component being configured:
to be delivered to the subject's mitral valve, while disposed in a constrained configuration inside the delivery device, the plurality of links forming a straight elongate shape while disposed in the constrained configuration, and
upon being released from the delivery device, to loop around at least a portion of the mitral valve, by the links flexing with respect to one another; and
one or more ventricular components that are configured to be placed underneath leaflets of the mitral valve and to be coupled to the atrial component.

Inventive concept 13. A method for treating a subject with a diseased mitral valve, the method comprising:
placing a docking element into a left atrium of the subject, via an interatrial septum of the subject, by advancing the docking element in a lateral direction with respect to the left atrium;
without substantially rotating the docking element subsequent to the advancement of the docking element, deploying the docking element within the subject's left atrium, such that the docking element defines a ring that is disposed at a native mitral annulus of the subject; and
subsequent thereto,
inserting a prosthetic mitral valve apparatus to inside the ring; and
deploying the prosthetic mitral valve apparatus within the ring, such that the prosthetic mitral valve is anchored within the ring.

Inventive concept 14. The method according to inventive concept 13, wherein deploying the docking element within the subject's left atrium comprises deploying the docking element within the subject's left atrium such that the docking element does not contact tissue of the left atrium in a vicinity of junctions of the left atrium with pulmonary veins of the subject.

Inventive concept 15. The method according to inventive concept 13, wherein advancing the docking element in the lateral direction with respect to the left atrium comprises advancing the docking element in a direction that is parallel to a longitudinal axis of a frame of the docking element, and wherein deploying the docking element within the subject's left atrium comprises deploying the docking element within the subject's left atrium such that a plane defined by the ring is disposed parallel to the longitudinal axis of the frame.

Inventive concept 16. The method according to inventive concept 13, wherein deploying the docking element within the subject's left atrium, comprises deploying the docking element within the subject's left atrium such that no portion of the docking element extends through the subject's native mitral valve.

Inventive concept 17. The method according to inventive concept 13, wherein inserting the prosthetic mitral valve apparatus to inside the ring comprises leaving the docking element within the subject's left atrium in the deployed state for a period of at least one week, and, subsequent thereto, inserting the prosthetic mitral valve apparatus to inside the ring.

Inventive concept 18. The method according to any one of inventive concepts 13-17, wherein inserting the docking element comprises inserting the docking element the docking element including a frame having tissue-ingrowth elements coupled thereto, the tissue-ingrowth elements being configured to encourage tissue ingrowth with respect to the frame.

Inventive concept 19. The method according to inventive concept 18, wherein inserting the docking element comprises inserting the docking element, the tissue-ingrowth elements including fabric sheets with fibers disposed thereon, the fibers being disposed substantially perpendicularly with respect to the fabric sheets.

Inventive concept 20. The method according to any one of inventive concepts 13-17, wherein inserting the docking element comprises inserting the docking element, the docking element including a frame that is covered with a fabric layer.

Inventive concept 21. The method according to inventive concept 20, wherein inserting the docking element comprises inserting the docking element, the fabric layer defining holes therethrough, and wherein deploying the docking element within the subject's left atrium comprises deploying the docking element within the subject's left atrium such that holes are disposed in a vicinity of junctions of the left atrium with pulmonary veins of the subject.

Inventive concept 22. Apparatus for treating a subject with a diseased mitral valve, the apparatus comprising:
　a docking element comprising:
　　a frame, the docking element being configured to be placed into a left atrium of the subject, via an interatrial septum of the subject, by advancing the docking element in a lateral direction with respect to the left atrium, along a longitudinal axis of the frame;
　　a ring disposed laterally with respect to the frame, such that the ring is substantially parallel with the longitudinal axis of the frame; and
　a prosthetic mitral valve apparatus configured to be placed at least partially inside the docking element, and to become anchored to the docking element, at least partially by radially expanding against the ring.

Inventive concept 23. The apparatus according to inventive concept 22, wherein the frame comprises a plurality of struts, and wherein the ring is defined by at least some of the struts of the frame.

Inventive concept 24. The apparatus according to inventive concept 22, wherein the docking element is configured to be deployed within the subject's left atrium, such that the ring is disposed at a mitral valve annulus of the subject, and such that the longitudinal axis of the frame is substantially parallel to the subject's native mitral valve annulus.

Inventive concept 25. The apparatus according to inventive concept 22, wherein the docking element is configured to become deployed within the subject's left atrium, such that no portion of the docking element extends through the subject's native mitral valve.

Inventive concept 26. The apparatus according to any one of inventive concepts 22-25, wherein the frame comprises tissue-ingrowth elements coupled thereto, the tissue-ingrowth elements being configured to encourage tissue ingrowth with respect to the frame.

Inventive concept 27. The apparatus according to inventive concept 26, wherein the tissue-ingrowth elements comprise fabric sheets with fibers disposed thereon, the fibers being disposed substantially perpendicularly with respect to the fabric sheets.

Inventive concept 28. The apparatus according to any one of inventive concepts 22-25, further comprising a fabric layer that is configured to cover the frame.

Inventive concept 29. The apparatus according to inventive concept 28, wherein the fabric layer defines holes therethrough, the holes defined by the fabric layer being configured to be disposed in a vicinity of junctions of the left atrium with pulmonary veins of the subject, when the docking element is in an implanted state within the subject's left atrium.

Inventive concept 30. A method for treating a subject with a diseased mitral valve, the method comprising:
　inserting a docking element into a left atrium of the subject, the docking element including a ring;
　deploying the docking element within the subject's left atrium, such that at least a portion of the docking element is disposed within a left atrial appendage of the subject, and such that the ring is disposed at a mitral valve annulus of the subject; and
　subsequent thereto,
　　inserting a prosthetic mitral valve to inside the ring; and
　　deploying the prosthetic mitral valve within the ring, such that the prosthetic mitral valve is anchored within the ring.

Inventive concept 31. The method according to inventive concept 30, wherein deploying the docking element within the subject's left atrium comprises deploying the docking element within the subject's left atrium such that the docking element does not contact tissue of the left atrium in a vicinity of junctions of the left atrium with pulmonary veins of the subject.

Inventive concept 32. The method according to inventive concept 30, wherein the docking element includes a frame, wherein inserting the docking element comprises inserting the docking element into the subject's left atrium transseptally in a direction that is parallel to a longitudinal axis of the frame, and wherein deploying the docking element within the subject's left atrium comprises deploying the docking element within the subject's left atrium such that a plane defined by the ring is substantially parallel to the longitudinal axis of the frame.

Inventive concept 33. The method according to inventive concept 30, wherein the docking element includes a frame, wherein inserting the docking element comprises inserting the docking element into the subject's left atrium transseptally in a direction that is parallel to a longitudinal axis of the frame, and wherein deploying the docking element within the subject's left atrium comprises deploying the docking element within the subject's left atrium such that the longitudinal axis of the frame is substantially parallel to a plane defined by the subject's mitral valve annulus.

Inventive concept 34. The method according to inventive concept 30, wherein deploying the docking element within the subject's left atrium, comprises deploying the docking element within the subject's left atrium such that no portion of the docking element extends through the subject's native mitral valve.

Inventive concept 35. The method according to inventive concept 30, wherein inserting the prosthetic mitral valve apparatus to inside the ring comprises leaving the docking element within the subject's left atrium in the deployed state for a period of at least one week, and, subsequent thereto, inserting the prosthetic mitral valve apparatus to inside the ring Inventive concept 36. The method according to any one of inventive concepts 30-35, wherein inserting the docking element comprises inserting the docking element, the docking element including a frame having tissue-ingrowth elements coupled thereto, the tissue-ingrowth elements being configured to encourage tissue ingrowth with respect to the frame.

Inventive concept 37. The method according to inventive concept 36, wherein inserting the docking element comprises inserting the docking element, the tissue-ingrowth elements including fabric sheets with fibers disposed thereon, the fibers being disposed substantially perpendicularly with respect to the fabric sheets.

Inventive concept 38. The method according to any one of inventive concepts 30-35, wherein inserting the docking element comprises inserting the docking element, the docking element including a frame that is covered with a fabric layer.

Inventive concept 39. The method according to inventive concept 38, wherein inserting the docking element comprises inserting the docking element, the fabric layer defining holes therethrough, and wherein deploying the docking element within the subject's left atrium comprises deploying the docking element within the subject's left atrium such that holes are disposed in a vicinity of junctions of the left atrium with pulmonary veins of the subject.

Inventive concept 40. Apparatus for treating a subject with a diseased mitral valve, the apparatus comprising:
  a docking element configured to be inserted into a left atrium of the subject, the docking element comprising:
    a ring configured to be deployed at a mitral valve annulus of the subject; and
    a left-atrial-appendage anchor configured to become anchored within a left atrial appendage of the subject; and
  a prosthetic mitral valve apparatus configured to be placed at least partially inside the docking element, and to become anchored to the docking element, at least partially by radially expanding against the ring.

Inventive concept 41. The apparatus according to inventive concept 40, wherein the docking element comprises a frame that comprises a plurality of struts, and wherein the ring is defined by at least some of the struts of the frame.

Inventive concept 42. The apparatus according to inventive concept 40, wherein the docking element comprises a frame, and a plane defined by the ring is parallel to a longitudinal axis of the frame.

Inventive concept 43. The apparatus according to any one of inventive concepts 40-42, wherein the docking element comprises a frame having tissue-ingrowth elements coupled thereto, the tissue-ingrowth elements being configured to encourage tissue ingrowth with respect to the frame.

Inventive concept 44. The apparatus according to inventive concept 43, wherein the tissue-ingrowth elements comprise fabric sheets with fibers disposed thereon, the fibers being disposed substantially perpendicularly with respect to the fabric sheets.

Inventive concept 45. The apparatus according to any one of inventive concepts 40-42, wherein the docking element comprises a frame and a fabric layer disposed upon the frame.

Inventive concept 46. The apparatus according to inventive concept 45, wherein the fabric layer defines holes therethrough, the holes defined by the fabric layer being configured to be disposed in a vicinity of junctions of the left atrium with pulmonary veins of the subject, when the docking element is in a deployed state within the subject's left atrium.

Inventive concept 47. A method for treating a subject with a diseased mitral valve, the method comprising:
  inserting a docking element into a left atrium of the subject;
  deploying the docking element within the subject's left atrium, such that the docking element defines a spiral that extends from a mitral annulus of the subject until a roof of the subject's left atrium, and becomes anchored within the left atrium by exerting an outward radial force upon a wall of the subject's left atrium; and subsequent thereto,
    inserting a prosthetic mitral valve to inside a portion of the spiral that is disposed at the subject's mitral annulus; and
    deploying the prosthetic mitral valve within the portion of the spiral that is disposed at the subject's mitral annulus, such that the prosthetic mitral valve is anchored within the portion of the spiral that is disposed at the subject's mitral annulus.

Inventive concept 48. Apparatus for treating a subject with a diseased mitral valve, the apparatus comprising:
  a docking element configured to be placed inside a left atrium of the subject, the docking element being configured to define a spiral that extends from a mitral annulus of the subject until a roof of the subject's left atrium, and to become anchored within the left atrium by exerting an outward radial force upon a wall of the subject's left atrium; and a prosthetic mitral valve apparatus configured to be placed at least partially inside the docking element, and to become anchored to the docking element, at least partially by radially expanding against a portion of the spiral that is disposed at the subject's mitral annulus.

Inventive concept 49. A method for treating a subject with a diseased mitral valve, the method comprising:
  inserting into a subject's left atrium:
    a docking element; and
    a prosthetic mitral valve apparatus that includes prosthetic mitral valve leaflets;

deploying the docking element and the prosthetic mitral valve apparatus within the left atrium, such that the prosthetic mitral valve apparatus is anchored to the docking element;

holding open the prosthetic mitral valve leaflets, such that the prosthetic mitral valve leaflets do not occlude blood flow through the prosthetic mitral valve apparatus;

leaving the docking element and the prosthetic mitral valve apparatus within the subject's left atrium in the deployed state for a period of at least one week; and subsequent thereto, allowing the prosthetic mitral valve leaflets to close.

Inventive concept 50. The method according to inventive concept 49, wherein holding open the prosthetic mitral valve leaflets comprises holding open the prosthetic mitral valve leaflets using sutures, and wherein allowing the prosthetic mitral valve leaflets to close comprises removing the sutures.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for treating a subject with a diseased native atrioventricular valve, the apparatus comprising:
a docking element configured to be implanted within an atrium of the subject such that no portion of the docking element extends through the diseased native atrioventricular valve, the docking element being configured to become anchored to tissue of the atrium at least partially via ingrowth of the tissue of the atrium to the docking element, the docking element comprising:
a ring configured to be implanted in a vicinity of an annulus of the diseased native atrioventricular valve;
a frame extending upwardly from the ring, a height of the frame being at least 15 mm, the frame being configured to radially expand against an inner wall of the subject's atrium; and
a prosthetic atrioventricular valve apparatus configured:
subsequent to the ingrowth of the tissue of the atrium to the docking element having occurred, to be placed at least partially inside the ring of the docking element, and
to become anchored to the docking element, at least partially by radially expanding against the ring;
the docking element being configured such that, subsequent to the docking element being deployed within the subject's atrium until insertion of the prosthetic atrioventricular valve apparatus to inside the ring of the docking element, the docking element is configured to be deployed within the subject's atrium without a prosthetic valve implant structure being disposed between leaflets of the diseased native atrioventricular valve and the docking element.

2. The apparatus according to claim 1, wherein the diseased native atrioventricular valve includes a diseased native tricuspid valve, wherein the docking element is configured to be implanted within a right atrium of the subject, and wherein the prosthetic atrioventricular valve apparatus comprises a prosthetic tricuspid valve apparatus.

3. The apparatus according to claim 1, wherein the frame comprises a plurality of struts, and wherein the ring is defined by at least some of the struts of the frame.

4. The apparatus according to claim 1, wherein a plane defined by the ring is parallel to a longitudinal axis of the frame.

5. The apparatus according to claim 1, further comprising a fabric layer disposed upon at least a portion of the frame of the docking element.

6. The apparatus according to claim 1, wherein the frame of the docking element comprises tissue-ingrowth elements coupled thereto, the tissue-ingrowth elements being configured to encourage tissue ingrowth with respect to the frame.

7. The apparatus according to claim 6, wherein the tissue-ingrowth elements are configured to rub against the wall of the subject's atrium and to encourage tissue growth into the docking element.

8. The apparatus according to claim 6, wherein the tissue-ingrowth elements comprise fabric sheets with fibers disposed thereon, the fibers being disposed substantially perpendicularly with respect to the fabric sheets.

9. The apparatus according to claim 1, wherein the diseased native atrioventricular valve includes a diseased native mitral valve, wherein the docking element is configured to be implanted within a left atrium of the subject, and wherein the prosthetic atrioventricular valve apparatus comprises a prosthetic mitral valve apparatus.

10. The apparatus according to claim 9, wherein the docking element further comprises a left-atrial-appendage anchor configured to become anchored within a left atrial appendage of the subject.

11. The apparatus according to claim 9, wherein:
the docking element is configured to be placed into the subject's left atrium, via an interatrial septum of the subject, by advancing the docking element in a lateral direction with respect to the left atrium, along an axis of the frame; and
the ring is disposed laterally with respect to the frame, such that the ring is substantially parallel with the axis of the frame.

12. The apparatus according to claim 11, wherein the docking element is configured to be deployed within the subject's left atrium, such that the axis of the frame is substantially parallel to the subject's native mitral valve annulus.

13. The apparatus according to claim 9, further comprising a fabric layer disposed upon at least a portion of the frame of the docking element.

14. The apparatus according to claim 13, wherein the fabric layer defines holes therethrough, the holes defined by the fabric layer being configured to be disposed in a vicinity of junctions of the left atrium with pulmonary veins of the subject, when the docking element is in an implanted state within the subject's left atrium.

* * * * *